United States Patent
D'Halluin

(10) Patent No.: US 9,593,317 B2
(45) Date of Patent: Mar. 14, 2017

(54) METHODS AND MEANS TO MODIFY A PLANT GENOME AT A NUCLEOTIDE SEQUENCE COMMONLY USED IN PLANT GENOME ENGINEERING

(75) Inventor: Kathleen D'Halluin, Mariakerke (BE)

(73) Assignee: Bayer CropScience NV, Diegem (BE)

(*) Notice: Subject to any disclaimer, the term of this patent is extended or adjusted under 35 U.S.C. 154(b) by 950 days.

(21) Appl. No.: 13/700,807

(22) PCT Filed: Jun. 7, 2011

(86) PCT No.: PCT/EP2011/002894
§ 371 (c)(1),
(2), (4) Date: Jan. 16, 2013

(87) PCT Pub. No.: WO2011/154158
PCT Pub. Date: Dec. 15, 2011

(65) Prior Publication Data
US 2013/0111620 A1    May 2, 2013

Related U.S. Application Data

(60) Provisional application No. 61/356,214, filed on Jun. 18, 2010.

(30) Foreign Application Priority Data

Jun. 9, 2010 (EP) .................................... 10005926

(51) Int. Cl.
C12N 15/82 (2006.01)
C12N 9/22 (2006.01)
A01C 1/00 (2006.01)

(52) U.S. Cl.
CPC .................. *C12N 9/22* (2013.01); *A01C 1/00* (2013.01); *C12N 15/8213* (2013.01); *C12N 15/8273* (2013.01); *C12N 15/8274* (2013.01); *C12N 15/8275* (2013.01); *C12N 15/8277* (2013.01); *C12N 15/8286* (2013.01)

(58) Field of Classification Search
None
See application file for complete search history.

(56) References Cited

U.S. PATENT DOCUMENTS

| | | |
|---|---|---|
| 4,761,373 A | 8/1988 | Anderson et al. |
| 4,962,028 A | 10/1990 | Bedbrook et al. |
| 5,013,659 A | 5/1991 | Bedbrook et al. |
| 5,141,870 A | 8/1992 | Bedbrook et al. |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,352,605 A | 10/1994 | Fraley et al. |
| 5,378,824 A | 1/1995 | Bedbrook et al. |
| 5,463,175 A | 10/1995 | Barry et al. |
| 5,504,200 A | 4/1996 | Hall et al. |
| 5,561,236 A | 10/1996 | Leemans et al. |
| 5,605,011 A | 2/1997 | Bedbrook et al. |
| 5,608,152 A | 3/1997 | Kridl et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,776,760 A | 7/1998 | Barry et al. |
| 5,824,790 A | 10/1998 | Keeling et al. |
| 5,908,810 A | 6/1999 | Donn |
| 5,908,975 A | 6/1999 | Caimi et al. |
| 5,928,937 A | 7/1999 | Kakefuda et al. |
| 6,013,861 A | 1/2000 | Bird et al. |
| 6,130,367 A | 10/2000 | Kossmann et al. |
| 6,162,966 A | 12/2000 | Kossmann et al. |
| 6,207,880 B1 | 3/2001 | Kossmann et al. |
| 6,211,436 B1 | 4/2001 | Kossmann et al. |
| 6,245,968 B1 | 6/2001 | Boudec et al. |
| 6,255,561 B1 | 7/2001 | Kossman et al. |
| 6,255,563 B1 | 7/2001 | Emmermann et al. |
| 6,268,549 B1 | 7/2001 | Sailland et al. |
| 6,284,479 B1 | 9/2001 | Nichols |
| 6,307,124 B1 | 10/2001 | Kossmann et al. |
| 6,566,587 B1 | 5/2003 | Lebrun et al. |
| 6,590,141 B1 | 7/2003 | Frohberg |

(Continued)

FOREIGN PATENT DOCUMENTS

| | | |
|---|---|---|
| EP | 04077624.7 | 9/2004 |
| EP | 06009836.5 | 5/2006 |

(Continued)

OTHER PUBLICATIONS

An, Yong-Qiang, et al., Conserved Expression of the Arabidopsis ACT1 and ACT3 Actin Subclass in Organ Primordia and Mature Pollen, 1996, The Plant Cell, 8:15-30.

An, Yong-Qiang, et al., Strong, constitutive expression of the Arabidopsis ACT2/ACT8 actin subclass in vegetative tissues, 1996, The Plant Journal, 10: 107-121.

Arnould, Sylvain, et al., Engineering of Large numbers of highly specific homing endonucleases that induce recombination on novel DNA targets, 2005, Journal of Molecular Biology, 355(3): 443-458.

Baumlein, Helmut, et al., A novel seed protein gene from Vicia faba is developmentally regulated in transgenic tobacco and Arabidopsis plants, 1991, Mol Gen Genet, 225: 459-467.

(Continued)

*Primary Examiner* — Matthew Keogh

(57) ABSTRACT

Methods and means are provided to modify in a targeted manner the plant genome of transgenic plants comprising chimeric genes wherein the chimeric genes have a DNA element commonly used in plant molecular biology. Redesigned meganucleases to cleave such an element commonly used in plant molecular biology are provided.

9 Claims, 6 Drawing Sheets

(56) References Cited

U.S. PATENT DOCUMENTS

| | | | |
|---|---|---|---|
| 6,699,694 B1 | 3/2004 | Buttcher et al. |
| 6,734,341 B2 | 5/2004 | Singletary et al. |
| 6,768,044 B1 | 7/2004 | Boudec et al. |
| 6,791,010 B1 | 9/2004 | Frohberg |
| 6,794,558 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 6,951,969 B1 | 10/2005 | Loerz et al. |
| 7,112,665 B1 | 9/2006 | Leemans et al. |
| 7,399,621 B2 | 7/2008 | Hammer et al. |
| 7,405,347 B2 | 7/2008 | Hammer et al. |
| 7,488,866 B2 | 2/2009 | Hammer et al. |
| 7,504,561 B2 | 3/2009 | Hammer et al. |
| 7,534,937 B2 | 5/2009 | Hammer et al. |
| 7,538,262 B2 | 5/2009 | Hammer et al. |
| 7,659,376 B2 | 2/2010 | Hammer et al. |
| 7,674,958 B2 | 3/2010 | Peters et al. |
| 7,700,842 B2 | 4/2010 | Hammer |
| 7,807,881 B2 | 10/2010 | Hammer et al. |
| 7,834,249 B2 | 11/2010 | Schouten et al. |
| 7,910,805 B2 | 3/2011 | Duck et al. |
| 7,960,615 B2 | 6/2011 | Peters et al. |
| 7,960,616 B2 | 6/2011 | Heinrichs et al. |
| 7,989,679 B2 | 8/2011 | Koziel et al. |
| 8,003,854 B2 | 8/2011 | Peters et al. |
| 8,097,775 B2 | 1/2012 | Hammer et al. |
| 2002/0031826 A1 | 3/2002 | Nichols |
| 2003/0167529 A1 | 9/2003 | Landschutze |
| 2004/0073966 A1 | 4/2004 | Zink et al. |
| 2005/0257283 A1 | 11/2005 | Matringe et al. |
| 2006/0015966 A1 | 1/2006 | Landschutze |
| 2006/0168690 A1 | 7/2006 | Shibatani et al. |
| 2006/0282914 A1* | 12/2006 | D'Halluin ......... C12N 15/8213 800/278 |
| 2007/0117128 A1* | 5/2007 | Smith .................. C12N 9/22 435/6.12 |
| 2007/0169218 A1 | 7/2007 | Carr et al. |
| 2007/0289035 A1 | 12/2007 | Vande Berg et al. |
| 2007/0295251 A1 | 12/2007 | Heinrichs |
| 2008/0250533 A1 | 10/2008 | Frohberg |
| 2009/0126044 A1 | 5/2009 | Carozzi et al. |
| 2009/0151018 A1 | 6/2009 | Hammer et al. |
| 2009/0203075 A1 | 8/2009 | Hammer et al. |
| 2009/0227771 A1 | 9/2009 | Peters et al. |
| 2009/0241219 A1 | 9/2009 | Hammer et al. |
| 2009/0293155 A1* | 11/2009 | Paul ................. C12N 15/8213 800/288 |
| 2009/0313717 A1 | 12/2009 | Hernandez et al. |
| 2010/0050295 A1 | 2/2010 | D'Halluin et al. |
| 2011/0047646 A1 | 2/2011 | Manzanero |
| 2012/0255051 A1 | 10/2012 | Ruiter et al. |

FOREIGN PATENT DOCUMENTS

| | | |
|---|---|---|
| EP | 1999263 | 12/2008 |
| WO | 8402913 | 8/1984 |
| WO | 8910396 | 11/1989 |
| WO | 9113980 | 9/1991 |
| WO | 9213956 | 8/1992 |
| WO | 9214827 | 9/1992 |
| WO | 9404692 | 3/1994 |
| WO | 9404693 | 3/1994 |
| WO | 9409144 | 4/1994 |
| WO | 9411520 | 5/1994 |
| WO | 9418313 | 8/1994 |
| WO | 9421795 | 9/1994 |
| WO | 9504826 | 2/1995 |
| WO | 9506128 | 3/1995 |
| WO | 9507355 | 3/1995 |
| WO | 9509233 | 4/1995 |
| WO | 9513389 | 5/1995 |
| WO | 9526407 | 10/1995 |
| WO | 9531553 | 11/1995 |
| WO | 9535026 | 12/1995 |
| WO | 9601904 | 2/1996 |
| WO | 9606932 | 3/1996 |
| WO | 9614408 | 5/1996 |
| WO | 9619581 | 6/1996 |
| WO | 9621023 | 7/1996 |
| WO | 9633270 | 10/1996 |
| WO | 9634968 | 11/1996 |
| WO | 9713865 | 4/1997 |
| WO | 9720936 | 6/1997 |
| WO | 9745545 | 12/1997 |
| WO | 9747806 | 12/1997 |
| WO | 9747807 | 12/1997 |
| WO | 9747808 | 12/1997 |
| WO | 9820145 | 5/1998 |
| WO | 9822604 | 5/1998 |
| WO | 9827212 | 6/1998 |
| WO | 9832326 | 7/1998 |
| WO | 9839460 | 9/1998 |
| WO | 9840503 | 9/1998 |
| WO | 9845461 | 10/1998 |
| WO | 9912950 | 3/1999 |
| WO | 9924593 | 5/1999 |
| WO | 9953072 | 10/1999 |
| WO | 9966050 | 12/1999 |
| WO | 0004173 | 1/2000 |
| WO | 0011192 | 3/2000 |
| WO | 0014249 | 3/2000 |
| WO | 0046386 | 8/2000 |
| WO | 0047727 | 8/2000 |
| WO | 0066746 | 11/2000 |
| WO | 0066747 | 11/2000 |
| WO | 0073422 | 12/2000 |
| WO | 0077229 | 12/2000 |
| WO | 0114569 | 3/2001 |
| WO | 0119975 | 3/2001 |
| WO | 0124615 | 4/2001 |
| WO | 0141558 | 6/2001 |
| WO | 0166704 | 9/2001 |
| WO | 0198509 | 12/2001 |
| WO | 0226995 | 4/2002 |
| WO | 0236782 | 5/2002 |
| WO | 02034923 | 5/2002 |
| WO | 02046387 | 6/2002 |
| WO | 02079410 | 10/2002 |
| WO | 02101059 | 12/2002 |
| WO | 03013226 | 2/2003 |
| WO | 03033540 | 4/2003 |
| WO | 03071860 | 9/2003 |
| WO | 03080809 | 10/2003 |
| WO | 03092360 | 11/2003 |
| WO | 2004040012 | 5/2004 |
| WO | 2004056999 | 7/2004 |
| WO | 2004067736 | 8/2004 |
| WO | 2004078983 | 9/2004 |
| WO | 2004090140 | 10/2004 |
| WO | 2004106529 | 12/2004 |
| WO | 2005002359 | 1/2005 |
| WO | 2005012515 | 2/2005 |
| WO | 2005020673 | 3/2005 |
| WO | 2005030941 | 4/2005 |
| WO | 2005030942 | 4/2005 |
| WO | 2005049842 | 6/2005 |
| WO | 2005093093 | 10/2005 |
| WO | 2005095617 | 10/2005 |
| WO | 2005095618 | 10/2005 |
| WO | 2005095619 | 10/2005 |
| WO | 2005095632 | 10/2005 |
| WO | 2005123927 | 12/2005 |
| WO | 2006007373 | 1/2006 |
| WO | 2006015376 | 2/2006 |
| WO | 2006018319 | 2/2006 |
| WO | 2006024351 | 3/2006 |
| WO | 2006032538 | 3/2006 |
| WO | 2006045633 | 5/2006 |
| WO | 2006060634 | 6/2006 |
| WO | 2006063862 | 6/2006 |
| WO | 2006072603 | 7/2006 |
| WO | 2006103107 | 10/2006 |

(56) References Cited

FOREIGN PATENT DOCUMENTS

| | | |
|---|---|---|
| WO | 2006105946 | 10/2006 |
| WO | 2006108702 | 10/2006 |
| WO | 2006129204 | 12/2006 |
| WO | 2006133827 | 12/2006 |
| WO | 2007002433 | 1/2007 |
| WO | 2007009823 | 1/2007 |
| WO | 2007024782 | 3/2007 |
| WO | 2007027777 | 3/2007 |
| WO | 2007035650 | 3/2007 |
| WO | 2007039314 | 4/2007 |
| WO | 2007039316 | 4/2007 |
| WO | 2007047859 | 4/2007 |
| WO | 2007049095 | 5/2007 |
| WO | 2007049156 | 5/2007 |
| WO | 2007074405 | 7/2007 |
| WO | 2007080126 | 7/2007 |
| WO | 2007080127 | 7/2007 |
| WO | 2007093836 | 8/2007 |
| WO | 2007103567 | 9/2007 |
| WO | 2007107302 | 9/2007 |
| WO | 2007107326 | 9/2007 |
| WO | 2007128052 | 11/2007 |
| WO | 2008017518 | 2/2008 |
| WO | 2008037436 | 4/2008 |
| WO | 2008080630 | 7/2008 |
| WO | 2008080631 | 7/2008 |
| WO | 2008090008 | 7/2008 |
| WO | 2008102199 | 8/2008 |
| WO | 2008148559 | 12/2008 |
| WO | 2008150473 | 12/2008 |
| WO | 2009111263 | 9/2009 |
| WO | 2009114321 | 9/2009 |
| WO | 2009144079 | 12/2009 |
| WO | 2009149787 | 12/2009 |

OTHER PUBLICATIONS

Beck, E., et al., Nucleotide sequence and exact localization of the neomycin phosphotransferase gene from transposon Tn5, 1982, Gene, 19(3): 327-336.

Benfey, Philip N., et al., The CaMV 35S enhancer contains at least two domains which can confer different developmental and tissue-specific expression patterns, 1989, EMBO Journal, 8: 2195-2202.

Bustos, Mauricio M., et al., Regulation of B-Glucuronidase expression in transgenic tobacco plants by an A/T-Rich, cis-Acting sequence found upstream of a franch bean b-phaseolin gene, 1989, The Plant Cell, 1: 839-853.

Carrington, James C., et al., Cap-Independent Enhancement of translation by a plant potyvirus 5' nontranslated region, 1990, Journal of Virology, 64(4): 1590-1597.

Chaboute, Marie-Edith, et al., Genomic organization and nucleotide sequences of two histone H3 and two histone H4 genes of Arabidopsis thaliana, 1987, Plant Molecular Biology, 8: 179-191.

Chilton, Mary-Dell M., et al., Targeted integration of T-DNA into the tobacco genome at double-stranded breaks: new insights on the mechanism of T-DNA integration, 2003, Plant Physiology, 133: 956-965.

Christensen, Alan H., et al., Maize polyubiquitin genes: structure, thermal perturbation of expression and transcript splicing, and promoter activity following transfer to protoplasts by electroporation, 1992, Plant Molecular Biology, 18: 675-689.

Comai, et al., An altered aroA Gene product confers resistance to the herbicide glyphosate, 1983, Science, 221: 370-371.

Crickmore, N., et al., Revision of the nomenclature for the bacillus thuringiensis pesticidal crystal proteins, 1998, Microbiology and Molecular Biology Review, 62(3): 807-813.

Degreve, H., et al., Nucleotide sequence and transcript map of the agrobacterium tumefaciens Ti plasmid-encoded octopine synthase gene, 1983, Journal of Molecular and Applied Genetics, 1:499-511.

Depicker, A., et al., Nopaline synthase; transcript mapping and DNA sequence, 1982, Journal of Molecular and Applied Genetics, 1: 561-573.

Dhaese, Patrick, et al., Identification of sequences involved in the polyadenylation of higher plant nuclear transcripts using Agrobacterium T-DNA genes as models, 1983, EMBO Journal, 2: 419-426.

D'Halluin, Kathleen, et al., Homologous recombination: a basis for targeted genome optimization in crop species such as maize, 2008, Plant Biotechnology Journal, 6: 93-102.

Gao, Huirong, et al., Heritable targeted mutagenesis in maize using a designed endonuclease, 2010, The Plant Journal, 61: 176-187.

Gasser, Charles S., et al., Structure, expression and evolution of the 5-enolpyruvylshikimate-3-phosphate synthase genes of petunia and tomato, 1988, The Journal of Biological Chemistry, 263: 4280-4289.

Harpster, Mark H., et al., Relative strengths of the 35S califlower mosaic virus, 1', 2', and nopaline synthase promoters in transformed tobacco sugarbeet and oilseed rape callus tissue, 1988, Mol Gen. Genet, 212: 182-190.

Holtorf, Sonke, et al., Comparison of different constitutive and inducible promoters for the overexpression of transgenes in Arabidopsis thaliana, 1995, Plant Molecular Biology, 29: 637-646.

Hudspeth, Richard L., et al., Structure and expression of the maize gene encoding the phosphoenolpyruvate carboxylase isozyme involved in C4 photosynthesis, 1989, Plant Molecular Biology, 12: 579-589.

Isalan, Mark, et al., A rapid, generally applicable method to engineer zinc fingers illustrated by targeting the HIV-1 promoter, 2001, Nature Biotechnology, 19: 656-660.

Josefsson, Lars-Goran, et al., Structure of a gene encoding the 1.7 S storage protein, napin, from Brassica napus, 1987, The Journal of Biological Chemistry, 262: 12196-12201.

Kalderon, Daniel, et al., A short amino acid sequence able to specify nuclear location, 1984, Cell, 39: 499-509.

Kaster, Kevin R., et al., Analysis of a bacterial hygromycin B resistance gene by transcriptional and translational fusions and by DNA sequencing, 1983, Nucleic Acids Research, 11: 6895-6911.

Keil, Michael, et al., Both wound-inducible and tuber-specific expression are mediated by the promoter of a single member of the potato proteinase inhibitor II gene family, 1989, EMBO Journal, 8(5): 1323-1330.

Keller, Beat, et al., Glycine-rich cell wall proteins in bean: gene structure and association of the protein with the vascular system, 1988, EMBO Journal, 7(2): 3625-3633.

Keller, Beat, et al., Specific expressional of a novel cell wall hydroxyproline-rich glycoprotein gene in lateral root initiation, nitiation, 2010, Genes and Development, 1989, 3: 1639-1646.

Krebbers, Enno, et al., Four genes in two diverged subfamilies encode the ribulose-1, 5-bishophate carboxylase small subunit polypeptides of Arabidopsis thaliana, 1988, Plant Molecular Biology, 11:745-759.

Kumar, Sandeep, et al., Controlling transgene integration in plants, 2001, Trends in Plant Science, 6: 155-159.

Liu, Qiang, et al., Design of polydactyl zinc-finger proteins for unique addressing within complex genomes, 1997, Proc. Natl. Acad. Sci, 94: 5525-5530.

McElroy, David, et al., Isolation of an Efficient actin promoter for use in rice transformation, 1990, The Plant Cell, 2: 163-171.

Moellenbeck, Daniel J., et al., Insecticidal proteins from Bacillus thuringiensis protect corn from corn rootworms, 2001, Nature Biotechnology, 19: 668-672.

Needleman, Saul B., et al., A General method applicable to the search for similarities in the amino acid sequence of two proteins, 1970, J. Mol. Biol., 48: 443-453.

Odell, T., et al., Identification of DNA sequences required for activity of the cauliflower mosaic virus 35S promoter, 1985, Nature, 313: 810-812.

Peleman, Johan, et al., Structure and expression analyses of the S-adenosylmethionine synthetase gene family in Arabidopsis thaliana, 1989, Gene, 84: 359-369.

Puchta, Holger, et al., Two different but related mechanisms are used in plants for the repair of genomic double-strand breaks by homologous recombination, 1996, Proc. Natl. Acad. Sci, 93: 5055-5060.

(56) References Cited

OTHER PUBLICATIONS

Raikhel, Natasha, et al., Nuclear targeting in plants, 1992, Plant Physiol. 100: 1627-1632.

Richins, Richard D., et al., Sequence of figwort mosaic virus DNA (caulimovirus group), 1987, Nucleic Acids Research, 15: 8451-8466.

Sanfacon, Helene, et al., A dissection of the cauliflower mosaic virus polyadenylation signal, 2010, Genes & Development, 5: 141-149.

Schnepf, H. Ernest, et al., Characterization of Cry34/Cry35 binary insecticidal proteins from diverse bacillus thuringiensis strain collections, 2005, Applied and environmental Microbiology, 71: 1765-1774.

Seligman, Lenny M., et al., Mutations altering the cleavage specificity of a homing endonuclease, 2002, Nucleic Acids Research, 30: 3870-3879.

Shah, Dilip M., et al., Engineering herbicide tolerance in transgenic plants, 1986, Science, 233: 478-481.

Shirsat, Anil, et al., Sequences responsible for the tissue specific promoter activity of a pea legumin gene in tobacco, 1989, Mol. Gen. Genet, 215: 326-331.

Stalberg, Kjell, et al., Disruption of an overlapping E-box/ABRE motif abolished high transcription of the napA storage-protein promoter in transgenic Brassica napus seeds, 1996, Planta, 199: 515-519.

Sussman, Django, et al., Isolation and characterization of new homing endonuclease specificities at individual target site positions, 2004, J. Mol. Biol. 342: 31-41.

Takagi, Hidenori, et al., Biochemical safety evaluation of transgenic rice seeds expressing T cell epitopes of Japanese cedar pollen allergens, 2006, J. Agric. Food Chem., 54: 9901-9905.

Thompson, Charles J., et al., Characterization of the herbicide-resistance gene bar from streptomyces hygroscopicus, 1987, EMBO Journal, 6: 2519-2523.

Thompson, Andrew J., et al., Cleavage and recognition patter of a double-strand-specific endonuclease (I-CreI) encoded by the chloroplast 23S rRNA intron of chlamydomonas reinhardtii, 1992, Gene, 119: 247-251.

Tranel, Patrick J., et al., Resistance of weeds to ALS-inhibiting herbicides: what have we learned?, 2002, Weed Science, 50: 700-712.

Verdaguer, Bertrand, et al., Isolation and expression in transgenic tobacco and rice plants, of the cassava vein mosaic virus (CVMV) promoter, 1996, Plant Molecular Biology, 31: 1129-1139.

Verdaguer, Bertrand, et al., Functional organization of the cassava vein mosaic virus (CsVMV) promoter, 1998, Plant Molecular Biology, 37: 1055-1067.

Wehrkamp-Richter, Sophie, et al., Characterisation of a new reporter system allowing high throughput in planta screening for recombination events before and after controlled DNA double strand break induction, 2009, Plant Physiology and Biochemistry, 47: 248-255.

Wohlleben, W., et al., Nucleotide sequence of the phosphinothricin N-acetyltransferase gene from streptomyces virido-chromogenes T8494 and its expression in Nicotiana tabacum, 1988, Gene, 70(1): 25-37.

Genbank Accession No. X05822, submitted Feb. 10, 1999.

Genbank Accession No. V00618, submitted Apr. 10, 2005.

International Search Report and Written Opinion for PCT/EP2011/002894, mailed Dec. 15, 2011.

\* cited by examiner

```
Met Ala Pro Lys Lys Lys Arg Lys Val His Met Asn Thr Lys Tyr Asn
1               5                   10                  15
Lys Lys Phe Leu Leu Tyr Leu Ala Gly Phe Val Asp Gly Asp Gly Ser
            20                  25                  30
Ile Lys Ala Gln Ile Ser Pro Glu Gln Ser Arg Lys Phe Lys His Arg
        35                  40                  45
Leu Arg Leu Thr Phe Gln Val Thr Gln Lys Thr Gln Arg Arg Trp Phe
    50                  55                  60
Leu Asp Lys Leu Val Asp Lys Ile Gly Val Gly Lys Val Tyr Asp Ser
65                  70                  75                  80
Gly Ser Val Ser Asp Tyr Ile Leu Ser Gln Ile Lys Pro Leu His Asn
                85                  90                  95
Phe Leu Thr Gln Leu Gln Pro Phe Leu Lys Leu Lys Gln Lys Gln Ala
            100                 105                 110
Asn Leu Val Leu Lys Ile Ile Glu Gln Leu Pro Ser Ala Lys Glu Ser
        115                 120                 125
Pro Asp Lys Phe Leu Glu Val Cys Thr Trp Val Asp Gln Ile Ala Ala
    130                 135                 140
Leu Asn Asp Ser Lys Thr Arg Lys Thr Ser Glu Thr Val Arg Ala
145                 150                 155                 160
Val Leu Asp Ser Leu Ser Glu Lys Lys Lys Lys Ser Ser Pro
                165                 170
```

Figure 3

```
Met Ala Pro Lys Lys Lys Arg Lys Val His Met Asn Thr Lys Tyr Asn
1               5                   10                  15
Glu Glu Phe Leu Leu Tyr Leu Ala Gly Phe Val Asp Gly Asp Gly Ser
            20                  25                  30
Ile Ile Ala Gln Ile Lys Pro Asn Gln Ser Cys Lys Phe Lys His Gln
        35                  40                  45
Leu Met Leu Thr Phe Gln Val Thr Gln Lys Thr Gln Arg Arg Trp Phe
    50                  55                  60
Leu Asp Glu Leu Val Asp Glu Ile Gly Val Gly Lys Val Tyr Asp Arg
65                  70                  75                  80
Gly Ser Val Ser Asp Tyr Arg Leu Cys Gln Ile Lys Pro Leu His Asn
            85                  90                  95
Phe Leu Thr Gln Leu Gln Pro Phe Leu Glu Leu Lys Gln Lys Gln Ala
        100                 105                 110
Asn Leu Val Leu Lys Ile Ile Gln Leu Pro Ser Ala Lys Glu Ser
        115                 120                 125
Pro Asp Lys Phe Leu Glu Val Cys Thr Trp Val Asp Gln Ile Ala Ala
    130                 135                 140
Leu Asn Asp Ser Lys Thr Arg Lys Thr Thr Ser Glu Thr Val Arg Ala
145                 150                 155                 160
Val Leu Asp Ser Leu Ser Glu Lys Lys Lys Lys Ser Ser Pro
                165                 170
```

Figure 4

```
Met Ala Pro Lys Lys Lys Arg Lys Val His Met Asn Thr Lys Tyr Asn
1               5                   10                  15
Lys Glu Phe Leu Leu Tyr Leu Ala Gly Phe Val Asp Gly Asp Gly Ser
            20                  25                  30
Ile Ile Ala Gln Ile Lys Pro Asn Gln Ser Cys Lys Phe Lys His Gln
        35                  40                  45
Leu Met Leu Thr Phe Gln Val Thr Gln Lys Thr Gln Lys Arg Arg Trp Phe
    50                  55                  60
Leu Asp Lys Leu Val Asp Glu Ile Gly Val Gly Lys Val Tyr Asp Arg
65                  70                  75                  80
Gly Ser Val Ser Asp Tyr Arg Leu Cys Gln Ile Lys Pro Leu His Asn
                85                  90                  95
Phe Leu Thr Gln Leu Gln Pro Phe Leu Lys Leu Lys Gln Lys Gln Ala
            100                 105                 110
Asn Leu Val Leu Lys Ile Ile Glu Val Cys Thr Arg Leu Pro Ser Ala Lys Glu Ser
        115                 120                 125
Pro Asp Lys Phe Leu Glu Val Cys Thr Trp Val Asp Gln Ile Ala Ala
    130                 135                 140
Leu Asn Asp Ser Lys Thr Arg Lys Thr Thr Ser Glu Thr Val Arg Ala
145                 150                 155                 160
Val Leu Asp Ser Leu Pro Gly Ser Val Gly Leu Ser Pro Ser Gln
                165                 170                 175
Ala Ser Ser Ala Ala Ser Ser Ala Ser Ser Ser Pro Gly Ser Gly Ile
        180                 185                 190
Ser Glu Ala Leu Arg Ala Gly Ala Thr Lys Ser Lys Glu Phe Leu Leu
    195                 200                 205
```

Tyr Leu Ala Gly Phe Val Asp Gly Asp Gly Ser Ile Lys Ala Gln Ile
        210                 215                 220

Ser Pro Glu Gln Ser Arg Lys Phe Lys His Arg Leu Arg Leu Thr Phe
    225                 230                 235                 240

Gln Val Thr Gln Lys Thr Gln Arg Arg Trp Phe Leu Asp Lys Leu Val
        245                 250                 255

Asp Glu Ile Gly Val Gly Lys Val Tyr Asp Ser Gly Ser Val Ser Asp
        260                 265                 270

Tyr Ile Leu Ser Gln Ile Lys Pro Leu His Asn Phe Leu Thr Gln Leu
    275                 280                 285

Gln Pro Phe Leu Lys Leu Lys Gln Ala Asn Leu Val Leu Lys
    290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
        325                 330                 335

Thr Arg Lys Thr Ser Glu Thr Val Arg Ala Val Leu Asp Ser Leu
    340                 345                 350

Ser Glu Lys Lys Lys Ser Ser Pro
    355                 360

Figure 5 continued

METHODS AND MEANS TO MODIFY A PLANT GENOME AT A NUCLEOTIDE SEQUENCE COMMONLY USED IN PLANT GENOME ENGINEERING

CROSS-REFERENCE TO RELATED APPLICATIONS

This application is a §371 U.S. National Stage of International Application No. PCT/EP2011/002894, filed Jun. 7, 2011, which claims the benefit of European Patent Application Serial No. 10005926.0, filed Jun. 9, 2010 and U.S. Patent Application Ser. No. 61/356,214, filed Jun. 18, 2010, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS10-2009wo_ST25.txt", created on Jun. 1, 2011, and having a size of 32,000 bytes and is filed concurrently with the specification. The sequence listing contained in this ASCII formatted document is part of the specification and is herein incorporated by reference in its entirety.

FIELD OF THE INVENTION

The invention relates to the field of agronomy. More particularly, the invention provides methods and means to introduce a targeted modification, including insertion, deletion or substitution, at a precisely localized nucleotide sequence in the genome of a transgenic plant, wherein the nucleotide sequence is comprised within an element or DNA fragment commonly used in plant transgenes, such as a commonly used transcription termination and polyadenylation region. The modifications are triggered in a first step by induction of a double stranded break at the recognition nucleotide sequence using meganucleases derived from naturally occurring meganucleases which have been re-designed to recognize the recognition site and cleave it.

BACKGROUND ART

The need to introduce targeted modifications in plant genomes, including the control over the location of integration of foreign DNA in plants has become increasingly important, and several methods have been developed in an effort to meet this need (for a review see Kumar and Fladung, 2001, *Trends in Plant Science*, 6, pp 155-159). These methods mostly rely on the initial introduction of a double stranded DNA break at the targeted location.

Activation of the target locus and/or repair or donor DNA through the induction of double stranded DNA breaks via rare-cutting endonucleases, such as I-SceI. has been shown to increase the frequency of homologous recombination by several orders of magnitude. (Puchta et al., 1996, *Proc. Natl. Acad. Sci. U.S.A.*, 93, pp 5055-5060; Chilton and Que, *Plant Physiol.*, 2003; D'Halluin et al. 2008 *Plant Biotechnol. J.* 6, 93-102). WO96/14408 describes an isolated DNA encoding the enzyme I-SceI. This DNA sequence can be incorporated in cloning and expression vectors, transformed cell lines and transgenic animals. The vectors are useful in gene mapping and site-directed insertion of genes.

WO00/46386 describes methods of modifying, repairing, attenuating and inactivating a gene or other chromosomal DNA in a cell through an I-SceI induced double strand break. Also disclosed are methods of treating or prophylaxis of a genetic disease in an individual in need thereof. Further disclosed are chimeric restriction endonucleases.

In addition, methods have been described which allow the design of rare cleaving endonucleases to alter substrate or sequence-specificity of the enzymes, thus allowing to induce a double stranded break at a locus of interest without being dependent on the presence of a recognition site for any of the natural rare-cleaving endonucleases. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO94/18313 or WO95/09233 and in Isalan et al., 2001, *Nature Biotechnology* 19, 656-660; Liu et al. 1997, *Proc. Natl. Acad. Sci. USA* 94, 5525-5530). Another way of producing custom-made meganucleases, by selection from a library of variants, is described in WO2004/067736. Custom made meganucleases or redesigned meganucleases with altered sequence specificity and DNA-binding affinity may also be obtained through rational design as described in WO2007/047859.

WO2007/049095 describes "LADGLIDADG" homing endonuclease variants having mutations in two separate subdomains, each binding a distinct part of a modified DNA target half site, such that the endonuclease variant is able to cleave a chimeric DNA target sequence comprising the nucleotides bound by each subdomain.

WO2007/049156 and WO2007/093836 describe I-CreI homing endonuclease variants having novel cleavage specificity and uses thereof.

WO2007/047859 describes rationally designed meganucleases with altered sequence specificity and DNA binding affinity.

WO2006/105946 described a method for the exact exchange in plant cells and plants of a target DNA sequence for a DNA sequence of interest through homologous recombination, whereby the selectable or screenable marker used during the homologous recombination phase for temporal selection of the gene replacement events can subsequently be removed without leaving a foot-print and without resorting to in vitro culture during the removal step, employing the therein described method for the removal of a selected DNA by microspore specific expression of a double stranded break inducing rare cleaving endonuclease.

U.S. provisional patent application 60/828,042 and European patent application 06020370.0, and WO2008/037436 describe variants of the methods and means of WO2006/105946 wherein the removal step of a selected DNA fragment induced by a double stranded break inducing rare cleaving endonuclease is under control of a germline-specific promoter. Other embodiments of the method relied on non-homologous endjoining at one end of the repair DNA and homologous recombination at the other end.

Gao et al. 2009, *The Plant Journal, pp* 1-11 describe heritable targeted mutagenesis in maize using a re-designed endonuclease.

Since the re-designed meganucleases are derived from naturally occurring endonucleases, the available potential recognition sites are not entirely random but appear to have some degree of resemblance to the nucleotide sequence originally recognized by the naturally occurring endonuclease upon which the re-designed meganuclease is based.

As stated by Gao et al, 2009 (supra) the structure-based protein design method to modify the DNA-binding characteristics of I-CreI are based on visual inspection of the I-CreI-DNA co-crystal structure leading to a prediction of a large number of amino acid substitutions that change I-CreI base preference at particular positions in its recognition site. Individual amino acid substitutions were evaluated experimentally, and those that conferred the desired change in base preference were added to a database of mutations that can be "mixed and matched" to generate derivatives of I-CreI that recognize highly divergent DNA sites. In theory, the combinatorial diversity available using the current mutation database is sufficient to target an engineered endonuclease approximately every 1000 bp in a random DNA sequence.

Accordingly, there still remains a need for functional re-designed meganucleases which can recognize a recognition site in an DNA element or region previously introduced into a transgenic plant as a commonly used part of a transgene, and induce a double branded DNA break in that region with sufficient efficiency, thereby triggering the events required for e.g. insertion of foreign DNA, deletion or substitution by homologous recombination or non-homologous endjoining at the double stranded break site. Identification of such a pair of recognition site and re-designed meganuclease, enhances the available tools to modify a plant genome in a targeted manner, by allowing insertion, deletion or substitution of the DNA in the vicinity of the induced double stranded DNA break at the location of a previously introduced transgene, without having to resort to presence of historically introduced recognition sites for rare-cleaving endonucleases such as e.g. I-SceI (which does not occur naturally in plant cells).

These and other problems are solved as described hereinafter in the different detailed embodiments of the invention, as well as in the claims.

SUMMARY OF THE INVENTION

In one embodiment of the invention, a method is provided for introducing a foreign DNA molecule at a predefined site in a genome of a transgenic plant cell comprising the steps of
  a. inducing a double stranded DNA break at the predefined site;
  b. introducing the foreign DNA molecule in the plant cell;
  c. selecting a plant cell wherein the foreign DNA is introduced at the predefined site; and
  d. optionally regenerating the plant cell into a plant
characterized in that the predefined site is a nucleotide sequence different from a recognition site for a natural occurring meganuclease and that the predefined site is a nucleotide sequence commonly introduced as part of a transgene in a transgenic plant and wherein double stranded DNA break is induced by introduction of a non-naturally occurring single chain meganuclease or a pair of non-naturally occurring meganucleases which recognizes or recognize in concert the predefined site and induces or induce the double stranded break.

In another embodiment the invention provides a method for introducing a foreign DNA molecule at a predefined site in a genome of a plant cell comprising the steps of
  a. inducing a double stranded DNA break at the predefined site;
  b. introducing the foreign DNA molecule in the plant cell;
  c. selecting a plant cell wherein the foreign DNA is introduced at the predefined site; and
  d. optionally regenerating the plant cell into a plant
characterized in that the predefined site is comprised within a 3' end termination and polyadenylation region of gene 7 of *Agrobacterium tumefaciens* octopine type T-DNA, which may have the nucleotide sequence of SEQ ID No 2 and that the double stranded DNA break is induced by introduction of a single chain meganuclease or a pair of meganucleases which recognizes or recognize in concert the predefined site and induces or induce the double stranded break. The predefined site may comprise the nucleotide sequence of SEQ ID No 1.

In yet another embodiment, a method is provided for introducing a foreign DNA molecule at a predefined site in a genome of a plant cell comprising the steps of
  a. inducing a double stranded DNA break at the predefined site;
  b. introducing the foreign DNA molecule in the plant cell;
  c. selecting a plant cell wherein the foreign DNA is introduced at the predefined site;
  d. optionally regenerating the plant cell into a plant
characterized in that the predefined site comprises the nucleotide sequence of SEQ ID No 1 and that the double stranded DNA break is induced by introduction of a single chain meganuclease or a pair of meganucleases which recognizes or recognize in concert the predefined site and induces or induce the double stranded break such as a meganuclease or the pair of meganucleases is/are derived from I-CreI and wherein the following amino acids are present in meganuclease unit 1: S at position 32; R at position 33; Q at position 80; R at position 40; K at position 66; Y at position 68; S at position 70; Q at position 44; K at position 24; S at position 28; E at position 30; and wherein the following amino acids are present in meganuclease unit 2: R at position 70; Q at position 44; Q at position 26; K at position 28; N at position 30; S at position 32; C at position 33; Q at position 38; Q at position 80; M at position 40; C at position 79; K at position 66; R at position 77; Y at position 68. Examples of such meganuclease are protein comprising the amino acid sequence of SEQ ID No. 4 and SEQ ID 5, respectively, or the single chain meganuclease comprises the amino acid sequence of SEQ ID 3 encoded by a nucleic acid comprising the nucleotide sequence of SEQ ID No. 3 from nucleotide position 2004 to nucleotide position 2525 or the nucleotide sequence of SEQ ID No. 3 from nucleotide position 4885 to nucleotide position 5405, or the single chain meganuclease is encoded by a nucleotide sequence comprising the nucleotide sequence of SEQ ID No 6 from position 1267 to position 1602 and from position 1796 to position 2544.

In any of the embodiments, the foreign DNA may be comprised within a repair DNA, the repair DNA comprising at least one flanking nucleotide sequence homologous to the upstream or downstream sequence of the nucleotide sequence of SEQ ID No. 1. The foreign DNA may comprises a selectable marker gene and/or a plant expressible gene of interest such as of a herbicide tolerance gene, an insect resistance gene, a disease resistance gene, an abiotic stress resistance gene, a enzyme involved in oil biosynthesis, carbohydrate biosynthesis, a enzyme involved in fiber strength or fiber length, an enzyme involved in biosynthesis of secondary metabolites. The foreign DNA may also be integrated as such, i.e. without flanking sequences with homology to the region around the predefined target site (without any further DNA), for integration by non-homologous end-joining.

The meganuclease or the pair of meganucleases may be expressed from a chimeric gene or a pair of chimeric genes, each comprising a plant expressible promoter operably linked to a coding region encoding the meganuclease or one of the pair of meganucleases, and further operationally linked to a DNA region involved in transcription termination and polyadenylation functional in a plant cell.

The invention further provides, plant cells and plants and seeds or propagating parts wherein the foreign DNA has been introduced into the predefined site, which have been obtained by the methods herein provided.

The invention also provides a method of growing a plant wherein the foreign DNA has been introduced into the predefined site, which has been obtained by the methods herein provided comprising the step of applying a chemical to the plant or substrate wherein the plant is grown.

Yet another embodiment of the invention concerns a process for producing a plant comprising foreign DNA integrated at the 3' end of gene 7 comprising the step of crossing a plant consisting essentially of the plant cells obtained by the methods of the invention with another plant or with itself and optionally harvesting seeds.

The invention also concerns a process comprising the step of applying a chemical compound on a plant or a seed of a plant wherein the foreign DNA has been introduced into the predefined site, which has been obtained by the methods herein provided.

Another embodiment of the invention relates to the use of a meganuclease or a pair of meganucleases as herein described to introduce a foreign DNA into the 3'end of gene 7 in a plant cell.

Yet another embodiment of the invention relates to the use of a custom made meganuclease to introduce a foreign DNA of interest at a predefined site in a plant cell.

BRIEF DESCRIPTION OF THE DRAWINGS

FIG. 3: Amino acid sequence of BAY 35 monomer (SEQ ID NO:4) (note that the amino acid sequence comprises a SV40 nuclear localization signal (amino acids 1 to 10)).

FIG. 4: Amino acid sequence of BAY 36 monomer (SEQ ID NO:5) (note that the amino acid sequence comprises a SV40 nuclear localization signal (amino acids 1 to 10))

FIG. 5: Amino acid sequence of BAY 35-36 single chain meganuclease (SEQ ID NO:9). (note that the amino acid sequence comprises a SV40 nuclear localization signal (amino acids 1 to 10); amino acids 11-166 correspond to BAY36; amino acids position 167 to 203 correspond to a linker signal; amino acids position 204-360 correspond to BAY 35).

DESCRIPTION OF DIFFERENT EMBODIMENTS OF THE INVENTION

Figure 1:
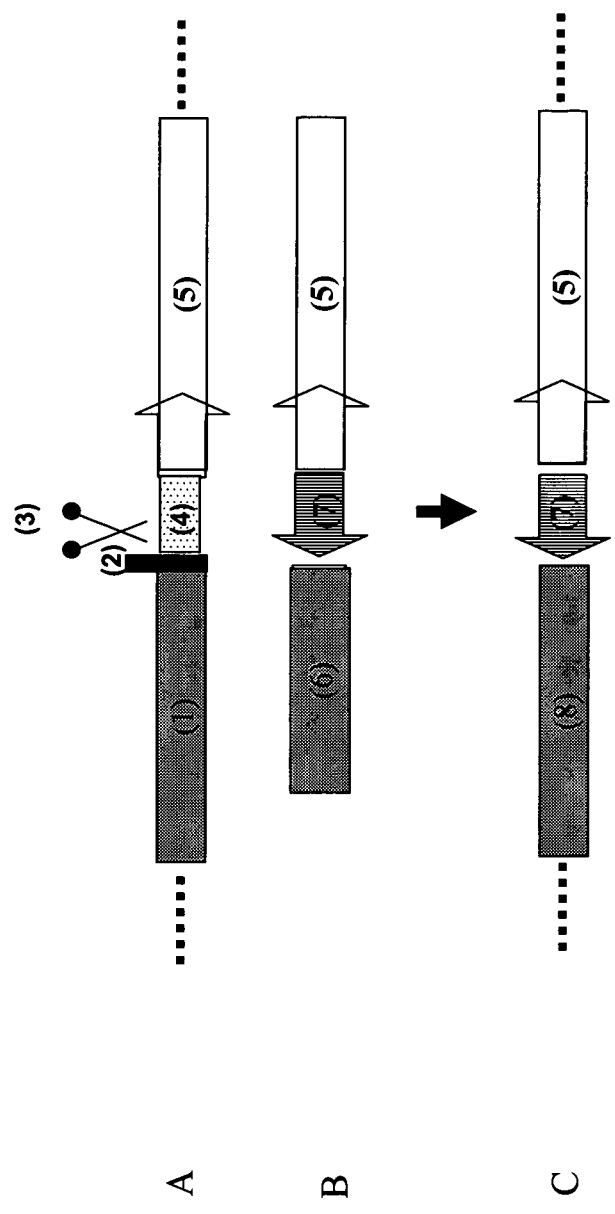
FIG. 1: is a schematic representation of target locus (A), the repair DNA (B) used in the assay for homologous recombination mediated targeted DNA insertion. The target locus after homologous recombination is also represented (C). (1) promoter less bar gene encoding 3' end of a phosphinotricin acetyl transferase; (2) I-SceI recognition site; (3) recognition site for BAY35/36 (either multimeric or single chain); (4) transcription termination and polyadenylation signal of A. tumefaciens gene 7 of the octopine type T-DNA.; (5): plant expressible neomycin phosphotransferase; (6) 5' end of the coding region of phosphinotricine acetyl transferase (7) promoter of the CaMV35S transcript; (8) restored complete coding region of phoshinotricin acetyltransferase.

The current invention is based on the observation that functional re-designed meganucleases can be obtained which specifically recognize and cleave a nucleotide sequence (SEQ ID No. 1—FIG. 2), which can be found in the nucleotide sequence of the plant functional transcription termination and polyadenylation region of gene 7 of the octopine type T-DNA vector (D'Haese et al, 1983, *The EMBO Journal*, 2, 419-426), at least when used in the right sequential context.

SEQ ID No. 2 represents the nucleotide sequence of the 3' end of gene 7 as it may be found in a number of chimeric plant-expressible genes, including pTTAM78 as described in Example 1. SEQ ID No. 2 differs from the nucleotide sequence as described in D'Haese et al. 1983 supra, in that the represented nucleotide strand of SEQ ID No 2 is the complement of the nucleotide sequence in D'Haese et al., and moreover is preceded by the nucleotide sequence "cggg". The recognition site of SEQ ID No. 1 corresponds to the nucleotide sequence of SEQ ID No. 2 from nucleotide 1 to 22. The herein described meganucleases are thus capable of recognizing and cleaving a nucleotide sequence in transgenic plants comprising a plant-expressible gene which has a plant expressible promoter operable linked to a transcribed DNA region of interest and followed by a 3' transcription termination and polyadenylation region having the nucleotide sequence which is the complement of the nucleotide sequence of SEQ ID No. 1, such as the complement of the nucleotide sequence of SEQ ID No. 2.

The 3'end of gene 7 has been incorporated in a number of transgenic plants which have been, are or will be commercialized including plants comprising the following events:

Oilseed rape (*Brassica napus*)
  Event MS1 as described in regulatory files DD95-04 (CA) or 98-278-01p (US)
  Event MS8 as described in regulatory files DD96-17 (CA) or 98-278-01p (US) or WO 2001/041558
  Event RF1 as described in regulatory files DD95-04 (CA) or 98-278-01p (US)
  Event RF2 as described in regulatory files DD95-04 (CA) or 98-278-01p (US)
  Event RF3 as described in regulatory files DD96-17 (CA) or 98-278-01p (US) or WO 2001/041558
Corn (*Zea mays*)
  B16 (=DLL25) as described in US deregulation dossier 95-145-01p or WO9506128
  DBT418 as described in US deregulation dossier 96-291-01p
  MON87460 as described in US deregulation dossier 09-055-01p, or WO 2009/111263 or as deposited in the ATCC collection under number PTA-8910
Rice (*Oryza sativa*)
  Event 7Crp#10 as described in Takagi et al., 2006, *Journal of Agricultural and Food Chemistry*, 54 (26), pp 9901-9905

Accordingly, in one embodiment, the invention relates to a method for introducing a foreign DNA molecule at a predefined or preselected site in a (nuclear) genome of a transgenic plant cell comprising the steps of
  a. inducing a double stranded DNA break at the predefined site;

b. introducing the foreign DNA molecule in said plant cell; and
c. selecting a plant cell wherein the foreign DNA is introduced at the predefined site;

wherein the predefined site is a nucleotide sequence different from a recognition site for a natural occurring meganuclease and is a nucleotide sequence commonly introduced as part of a transgene in a transgenic plant and wherein double stranded DNA break is induced by introduction of a non-naturally occurring single chain meganuclease or a pair of non-naturally occurring meganuclease monomeric units which recognizes or recognize together the predefined site and induces or induce the double stranded break.

As used herein, "a nucleotide sequence commonly introduced as a part of a transgene in plants" refers to a nucleotide sequence of a DNA region that has been used previously as an element of a chimeric gene introduced in plants, whereby transgenic plants are readily available, particularly whereby the transgenic plants have been, are or will be commercialized and regulatory approvals have been applied for and are publicly available. Several databases are available which summarize and provide information on applications for regulatory approvals including the GM crop database of the Center of Environmental risk assessment which can be consulted online (http://www.cera-gmc.org/?action=gm_crop_database&) or the summary list of the Petitions of Nonregulated Status Granted or Pending by APHIS, available online at http://www.aphis.usda.gov/brs/not_reg.html.

DNA regions commonly introduced as part of a transgene in plants include promoter regions such as the 35S promoter of the CaMV 35S transcript (Odell et al. (1985), *Nature* 313: 810-812); the FMV 35S promoter (Richins R. D., Scholthof H. B., Shepherd R. J. (1987) Sequence of the figwort mosaic virus (caulimovirus group). *Nucleic Acids Research* 15: 8451-8466); the promoter of the small subunit of *Arabidopsis thaliana* Rubisco gene (Krebbers E., Seurinck J., Herdies L., Cashmore A. R., Timko M. P. (1988). Four genes in two diverged subfamilies encode the ribulose-1,5-bisphosphate carboxylase small subunit polypeptides of *Arabidopsis thaliana*. *Plant Molecular Biology*, 11, 745-759); the Casava Vein Mosaic Virus promoter (Verdaguer et al (1996) *Plant Mol. Biol.* 31: 1129 or Verdaguer et al (1998) *Plant Mol. Biol.* 37: 1055); the Actin2 promoter from *Arabidopsis* (An Y. Q., McDowell J. M., Huang S., McKinney E. C., Chambliss S., Meagher R. B. (1996) Strong, constitutive expression of the *Arabidopsis* ACT2/ACT8 actin subclass in vegetative tissues. *The Plant Journal* 10: 107-121) or rice (McElroy D., Zhang W., Cao J., Wu R. (1990) Isolation of an efficient actin promoter for use in rice transfomation. *The Plant Cell* 2: 163-171); the Histone H3 promoter or histone H4 promoter (Chabouté M, Chaubet N, Philipps G, Ehling M and Gigot C (1987) Genomic organization and nucleotide sequences of two histone H3 and two histone H4 genes of *Arabidopsis thaliana*. *Plant Mol. Biol.* 8: 179-191); the promoter of the maize (*Zea mays*) ubiquitin-1 gene (Christensen et al (1992) *Plant Mol. Biol.* 18: 675); 5' UTR leader sequences such as the cab22L leader (Harpster M, Townsend J, Jones J, Bedbrook J and Dunsmuir P.(1988) Relative strengths of the 35S cauliflower mosaic virus, 1', 2' and nopaline synthase promoters in transformed tobacco, sugarbeet and oilseed rape callus tissue. *Mol Gen Genet.* 212:182-190); or 5' tev (Carrington J and Freed D (1990) Cap-independent enhancement of translation by a plant potyvirus 5' nontranslated region. *J Virol* 64(4): 1590-1597); a 3' end of the nopaline synthase gene (Depicker A., Stachel S., Dhaese P., Zambryski P., Goodman H. M. (1982). Nopaline synthase: transcript mapping and DNA sequence. *Journal of Molecular and Applied Genetics* 1, 561-573); a 3' end of the octopine synthase gene (De Greve H., Dhaese P., Seurinck J., Lemmers M., Van Montagu M., Schell J. (1982). Nucleotide sequence and transcript map of the *Agrobacterium tumefaciens* Ti plasmid-encoded octopine synthase gene. *Journal of Molecular and Applied Genetics*, 1, 499-511); the CaMV35S terminator (Sanfaçon et al (1991) *Genes Dev.* 5: 141) and selectable markers such as bar (Thompson, C., Movva, R., Tizard, R., Crameri, R., Davies, J., Lauwereys, M. ans Botterman, J. (1987) Characterization of the herbicide-resistance gene bar from *Streptomyces hygroscopicus*. *The EMBO Journal* 6: 2519-2523 (Accession X05822)); pat (Wohlleben, W., Arnold, W., Broer, I., Hillemann, D., Strauch, E. and Puhler, A. Nucleotide sequence of the phosphinothricin N-acetyltransferase gene from *Streptomyces viridochromogenes* Tu494 and its expression in *Nicotiana tabacum*. *Gene* 70 (1), 25-37 (1988)); 2mepsps (sequence 4 from U.S. Pat. No. 6,566,587 or EMBL number AR337832); CP4 (Padgette S. R., Re D., Barry G., Eichholtz D., Delannay X., Fuchs R. L., Kishore G. M., Fraley R. T. (1996). New weed control opportunities: development of soybeans with a Roundup Ready gene. In Herbicide-Resistant Crops: Agricultural, Environmental, Econ. . . . , neo Accession V00618; Beck et al (1982) *Gene* 19(3) p327-336); or hpt (Kaster et al., (1983), NAR 11, 6895-6911).

A preferred DNA region in the context of this invention is the nucleotide sequence of the plant functional transcription termination and polyadenylation region of gene 7 of the octopine type T-DNA vector (D'Haese et al, 1983, *The EMBO Journal*, 2, 419-426), as mentioned above.

The redesigned meganucleases described herein are based on the naturally occurring meganuclease I-CreI for use as a scaffold. I-CreI is a homing endonuclease found in the chloroplasts of *Chlamydomonas rheinhardti* (Thompson et al. 1992, *Gene* 119, 247-251). This endonuclease is a homodimer that recognizes a pseudo-palindromic 22 bp DNA site in the 23SrRNA gene and creates a double stranded DNA break that is used from the introduction of an intron. I-CreI is a member of a group endonucleases carrying a single LAGLIDADG (SEQ ID NO:10) motif. LAGLIDADG (SEQ ID NO:10) enzymes contain one or two copies of the consensus motif. Single-motif enzymes, such as I-CreI function as homodimers, whereas double-motif enzymes are monomers with two separate domains. Accordingly, when re-designing meganucleases derived from an I-CreI scaffold to recognize a 22 bp nucleotide sequence of interest, two monomeric units are designed, each recognizing a part of the 22 bp recognition site, which are needed in concert to induce a double stranded break at the 22 bp recognition site (WO2007/047859). Concerted action may be achieved by linking the two monomeric units into one single chain meganuclease, or may also be achieved by promoting the formation of heterodimers, as described e.g. in WO2007/047859.

The amino acid sequence of a naturally occurring I-CreI monomer is provided as SEQ ID No. 8. To re-design I-CreI monomeric units such that the heterodimers thereof recognize the nucleotide sequence of SEQ ID No. 1 the following amino acids were introduced at the mentioned positions:
1. in meganuclease unit 1:
   a. S at position 32;
   b. R at position 33;
   c. Q at position 80;
   d. R at position 40;
   e. K at position 66;
   f. Y at position 68;

g. S at position 70;
h. Q at position 44;
i. K at position 24;
j. S at position 28;
k. E at position 30;

2. in meganuclease unit 2:
l. R at position 70;
m. Q at position 44;
n. Q at position 26;
o. K at position 28;
p. N at position 30;
q. S at position 32;
r. C at position 33;
s. Q at position 38;
t. Q at position 80;
u. M at position 40;
v. C at position 79; and
w. K at position 66.

Figure 2:
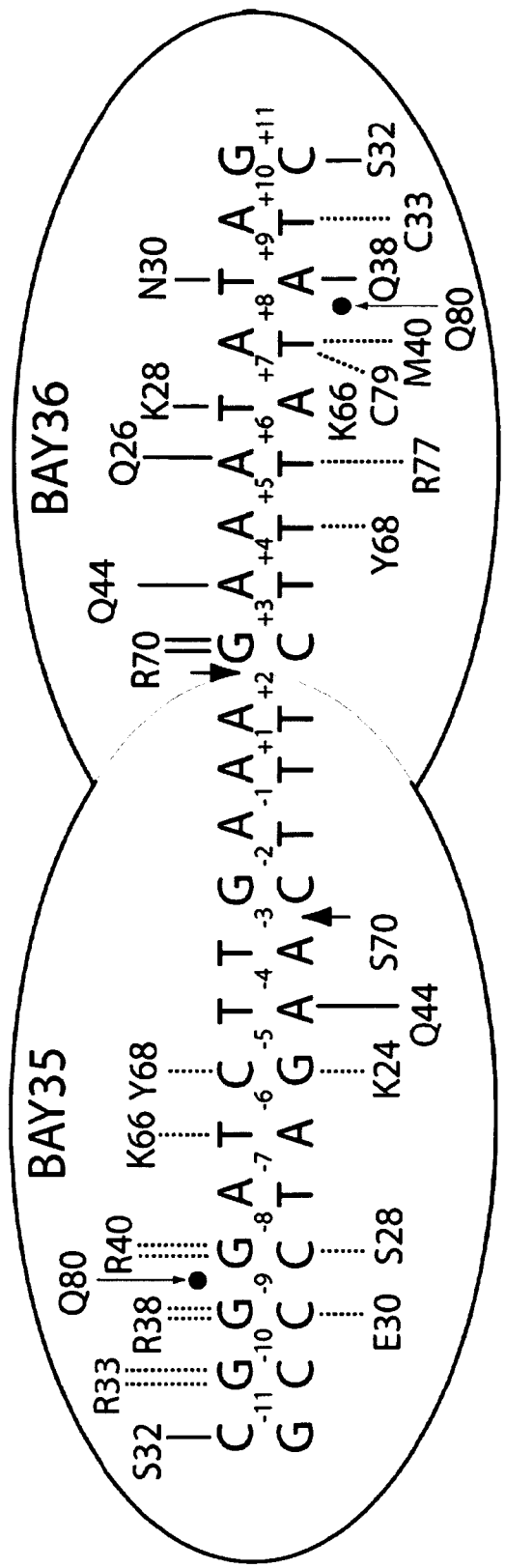
FIG. 2: Schematic representation of the recognition site (SEQ ID NO:1) and interactions with amino acids of the different meganuclease units BAY 35 and BAY36 (either as heterodimers or as a single chain meganuclease).

A schematic representation thereof is provided in FIG. 2. The re-designed double stranded break inducing enzyme may comprise, but need not comprise, a nuclear localization signal (NLS), such as the NLS of SV40 large T-antigen [Raikhel, Plant Physiol. 100: 1627-1632 (1992) and references therein] [Kalderon et al. Cell 39: 499-509 (1984)]. The nuclear localization signal may be located anywhere in the protein, but is conveniently located at the N-terminal end of the protein. The nuclear localization signal may replace one or more of the amino acids of the double stranded break inducing enzyme. It should be noted that if the re-designed meganuclease has been provided with a NLS at the N-terminus of the protein, such as a 10 or 12 amino acid NLS of SV40, the amino acid positions would be shifted (increased) accordingly. Likewise, in the event two monomeric units are linked into a single chain meganuclease, the position of the second unit will also be shifted. The corresponding amino acid positions with regard to the I-CreI amino acid sequence can also be identified by determining the optimal alignment as described below. It will be clear that in the single chain redesigned meganuclease the order of the units is irrelevant, i.e. whether the above unit 1 and 2 occur indeed within that order in the single amino acid chain or unit 2 precedes unit one in the single amino acid chain does not make a difference in order for the two units combined to be able to recognize the target sequence.

Re-designed meganucleases suitable for the invention may comprise an amino acid sequence as represented in SEQ ID No. 4 and 5 (monomeric units which can cleave the recognition site as a heterodimer) or SEQ ID No. 7 (single chain nuclease).

Conveniently, the redesigned meganuclease(s) can be provided by expression of a plant expressible recombinant gene(s) encoding such meganuclease(s). To this end, a DNA region comprising a nucleotide sequence encoding a re-designed meganuclease or meganuclease monomeric unit can be operably linked to a plant-expressible promoter and a DNA region involved in transcription termination and polyadenylation and introduced into a plant or plant cells. The recombinant gene(s) encoding redesigned meganuclease(s) may be introduced transiently or stably.

For the purpose of the invention, the term "plant-operative promoter" and "plant-expressible promoter" mean a promoter which is capable of driving transcription in a plant, plant tissue, plant organ, plant part, or plant cell. This includes any promoter of plant origin, but also any promoter of non-plant origin which is capable of directing transcription in a plant cell.

Promoters that may be used in this respect are constitutive promoters, such as the promoter of the cauliflower mosaic virus (CaMV) 35S transcript (Hapster et al., 1988, Mol. Gen. Genet. 212: 182-190), the CaMV 19S promoter (U.S. Pat. No. 5,352,605; WO 84/02913; Benfey et al., 1989, EMBO J. 8:2195-2202), the subterranean clover virus promoter No 4 or No 7 (WO 96/06932), the Rubisco small subunit promoter (U.S. Pat. No. 4,962,028), the ubiquitin promoter (Holtorf et al., 1995, Plant Mol. Biol. 29:637-649), T-DNA gene promoters such as the octopine synthase (OCS) and nopaline synthase (NOS) promoters from Agrobacterium, and further promoters of genes whose constitutive expression in plants is known to the person skilled in the art.

Further promoters that may be used in this respect are tissue-specific or organ-specific promoters, preferably seed-specific promoters, such as the 2S albumin promoter (Josefsson et al., 1987, J. Biol. Chem. 262:12196-12201), the phaseolin promoter (U.S. Pat. No. 5,504,200; Bustos et al., 1989, Plant Cell 1.(9):839-53), the legumine promoter (Shirsat et al., 1989, Mol. Gen. Genet. 215(2):326-331), the "unknown seed protein" (USP) promoter (Baumlein et al., 1991, Mol. Gen. Genet. 225(3):459-67), the napin promoter (U.S. Pat. No. 5,608,152; Stalberg et al., 1996, Planta 199:515-519), the Arabidopsis oleosin promoter (WO 98/45461), the Brassica Bce4 promoter (WO 91/13980), and further promoters of genes whose seed-specific expression in plants is known to the person skilled in the art.

Other promoters that can be used are tissue-specific or organ-specific promoters like organ primordia-specific promoters (An et al., 1996, Plant Cell 8: 15-30), stem-specific promoters (Keller et al., 1988, EMBO J. 7(12): 3625-3633), leaf-specific promoters (Hudspeth et al., 1989, Plant Mol. Biol. 12: 579-589), mesophyl-specific promoters (such as the light-inducible Rubisco promoters), root-specific promoters (Keller et al., 1989, Genes Dev. 3: 1639-1646), tuber-specific promoters (Keil et al., 1989, EMBO J. 8(5): 1323-1330), vascular tissue-specific promoters (Peleman et al., 1989, Gene 84: 359-369), stamen-selective promoters (WO 89/10396, WO 92/13956), dehiscence zone-specific promoters (WO 97/13865), and the like.

Nucleotide sequences encoding re-designed meganucleases suitable for the invention may comprise the nucleotide sequence of SEQ ID No. 3 from nucleotide position 2004 to nucleotide position 2525 or 2522, or the nucleotide sequence of SEQ ID No. 3 from nucleotide position 4885 to nucleotide position 5405 or 5403, or by a nucleotide sequence of SEQ ID No. 6 from position 1267 to position 1602 or 1605 and from position 1796 or 1765 to position 2544 or 2541. The linker is encoded by the nucleotide sequence of SEQ ID No. 6 from position 1957 to 2070. To facilitate cloning and other recombinant DNA techniques, it may be advantageous to include an intron functional in plants into the region encoding a meganuclease, particularly a single chain meganuclease, such as the ST-LS1 intron of SEQ ID No. 6 from position 1603 or 1606 to position 1795.

The DNA region encoding the re-designed meganuclease may be optimized for expression in plants by adapting GC content, codon usage, elimination of unwanted nucleotide sequences. The coding region may further be optimized for expression in plants and the synthetic coding region may have a nucleotide sequence which has been designed to fulfill the following criteria:

a) the nucleotide sequence encodes a functional redesigned homing endonuclease as herein described;
b) the nucleotide sequence has a GC content of about 50% to about 60%;

c) the nucleotide sequence does not comprise a nucleotide sequence selected from the group consisting of GATAAT, TATAAA, AATATA, AATATT, GATAAA, AATGAA, AATAAG, AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA and CATAAA;
d) the nucleotide does not comprise a nucleotide sequence selected from the group consisting of CCAAT, ATTGG, GCAAT and ATTGC;
e) the nucleotide sequence does not comprise a sequence selected from the group consisting of ATTTA, AAGGT, AGGTA, GGTA or GCAGG;
f) the nucleotide sequence does not comprise a GC stretch consisting of 7 consecutive nucleotides selected from the group of G or C;
g) the nucleotide sequence does not comprise a AT stretch consisting of 5 consecutive nucleotides selected from the group of A or T; and
h) the nucleotide sequence does not comprise codons coding for Leu, Ile, Val, Ser, Pro, Thr, Ala that comprise TA or CG duplets in positions 2 and 3 (i.e. the nucleotide sequence does not comprise the codons TTA, CTA, ATA, GTA, TCG, CCG, ACG and GCG).

An example of such an optimized sequence is represented by SEQ ID No. 6 from nucleotide position 1267 to position 1602 or 1605 and from position 1796 or 1795 to position 2544 or 2541 (wherein the nucleotide sequence encoding the linker present between the two meganuclease units is represented by nt 1957 to 2070).

It will also be clear that the terms used to describe the method such as "introduction of a DNA fragment" as well as "regeneration of a plant from the cell" do not imply that such DNA fragment necessarily needs to be introduced by transformation techniques. Indeed, it will be immediately clear to the person skilled in the art that the DNA molecule of interest may also be introduced by breeding or crossing techniques from one plant to another.

However, it will be clear that the DNA molecule of interest may be introduced into the plant cells by any method known in the art, including *Agrobacterium* mediated transformation but also by direct DNA transfer methods. The transforming DNA molecule can be transferred into plant cells using any conventional method, including but not limited to direct DNA transfer method. As used herein "direct DNA transfer" is any method of DNA introduction into plant cells which does not involve the use of natural *Agrobacterium* spp. and which is capable of introducing DNA into plant cells. This includes methods well known in the art such as introduction of DNA by electroporation into protoplasts, introduction of DNA by electroporation into intact plant cells or partially degraded tissues or plant cells, introduction of DNA through the action of agents such as PEG and the like, into protoplasts, use of silicon whiskers, and bombardment with DNA coated microprojectiles.

The capability of inducing a double stranded break at a preselected site opens up several potential applications. Foreign DNA of interest may be introduced into the preselected site either by homologous recombination, or in the process of non-homologous endjoining. The double stranded break may also be used to induce the formation of small deletions or insertions at the preselected site, thereby potentially inactivating the chimeric gene comprising the nucleotide sequence of the preselected site. The double stranded break at the preselected site will also facilitate replacement of a DNA region in the vicinity of that site for a DNA region of interest e.g. as described in WO 06/105946, WO08/037436 or WO08/148559.

To insert foreign DNA by homologous recombination at the preselected site, the foreign DNA may be comprised within a repair DNA, wherein the foreign DNA is flanked by at least one flanking DNA region having a nucleotide sequence which is similar to the nucleotide sequence of the DNA region upstream or downstream of the preselected site. The repair DNA may comprise the foreign DNA to be inserted flanked by two flanking DNA regions, upstream and downstream of the foreign DNA and which are similar to nucleotide sequence of the DNA region upstream or downstream of the preselected sites. Alternatively, the foreign DNA may be integrated as such, i.e. without flanking sequences with homology to the region around the predefined target site (without any further DNA), for integration by non-homologous end-joining.

As used herein "a flanking DNA region" is a DNA with a nucleotide sequences having homology to the DNA regions respectively upstream or downstream of the target DNA sequence or preselected site. This allows to better control the insertion of the foreign DNA or the DNA molecule of interest. Indeed, integration by homologous recombination will allow precise joining of the foreign DNA fragment to the plant nuclear genome up to the nucleotide level.

The flanking DNA regions may vary in length, and should be at least about 10 nucleotides in length. However, the flanking region may be as long as is practically possible (e.g. up to about 100-150 kb such as complete bacterial artificial chromosomes (BACs)). Preferably, the flanking region will be about 50 bp to about 2000 bp. Moreover, the regions flanking the foreign DNA of interest need not be identical to the DNA regions flanking the preselected site and may have between about 80% to about 100% sequence identity, preferably about 95% to about 100% sequence identity with the DNA regions flanking the preselected site. The longer the flanking region, the less stringent the requirement for homology. Furthermore, it is preferred that the sequence identity is as high as practically possible in the vicinity of the location of exact insertion of the foreign DNA. Furthermore, to achieve exchange of the target DNA sequence without changing the DNA sequence of the adjacent DNA sequences, the flanking DNA sequences should preferably be identical to the DNA regions flanking the preselected site.

Moreover, the regions flanking the foreign DNA of interest need not have homology to the regions immediately flanking the preselected site, but may have homology to a DNA region of the nuclear genome further remote from that preselected site. Insertion of the foreign DNA will then result in a removal of the target DNA between the preselected insertion site and the DNA region of homology. In other words, the target DNA located between the homology regions will be substituted for the foreign DNA of interest. Thus, by choosing the appropriate configuration of the foreign DNA for repair of the double stranded DNA break, by introducing a foreign DNA molecule according to the methods of the invention, in addition to insertions, one can also make targeted replacements or targeted deletions of the genomic region located between the homology regions.

The foreign DNA to be inserted may also comprise a selectable or screenable marker, which may or may not be removed after insertion.

"Selectable or screenable markers" as used herein have there usual meaning in the art and include, but are not limited to plant expressible phosphinotricin acetyltransferase, neomycine phosphotransferase, glyphosate oxidase, glyphosate tolerant EPSP enzyme, nitrilase gene, mutant acetolactate synthase or acetohydroxyacid synthase gene, β-glucoronidase (GUS), R-locus genes, green fluorescent protein and the likes.

The selection of the plant cell or plant wherein the selectable or screenable marker and the rest of the foreign DNA molecule has been introduced by homologous recombination through the flanking DNA regions can e.g. be achieved by screening for the absence of sequences present in the transforming DNA but located outside of the flanking DNA regions. Indeed, presence of sequences from the transforming DNA outside the flanking DNA regions would indicate that the origination of the transformed plant cells is by random DNA insertion. To this end, selectable or screenable markers may be included in the transforming DNA molecule outside of the flanking DNA regions, which can then be used to identify those plant cells which do not have the selectable or screenable markers located outside of the transforming DNA and which may have arisen by homologous recombination through the flanking DNA regions. Alternatively, the transforming DNA molecule may contain selectable markers outside the flanking DNA regions that allow selection for the absence of such genes (negative selectable marker genes).

It will be clear that the methods according to the invention allow insertion of any DNA of interest including DNA comprising a nucleotide sequence with a particular nucleotide sequence signature e.g. for subsequent identification. The DNA of interest may also be one or more plant expressible gene(s) including but not limited to a herbicide tolerance gene, an insect resistance gene, a disease resistance gene, an abiotic stress resistance gene, an enzyme involved in oil biosynthesis or carbohydrate biosynthesis, an enzyme involved in fiber strength and/or length, an enzyme involved in the biosynthesis of secondary metabolites.

Herbicide-tolerance genes include a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024782. Glyphosate-tolerant plants can also be obtained by selecting plants containing naturally-occurring mutations of the above-mentioned genes, as described in for example WO 01/024615 or WO 03/013226. EPSPS genes that confer glyphosate tolerance are described in e.g. U.S. patent application Ser. Nos 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide tolereance genes may encode an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Herbicide-tolerance genes may also confer tolerance to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, and WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide tolerance genes encode variant ALS enzymes (also known as acetohydroxyacid synthase, AHAS) as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerance genes are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerance gebnes are described in for example WO 07/024782 and U.S. Patent Application No. 61/288,958.

Insect resistance gene may comprise a coding sequence encoding:
1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214, 022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/ vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214, 022 and EP 08010791.5);

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein).

An "insect-resistant gene as used herein, further includes transgenes comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Abiotic stress tolerance genes include:

1) a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) a transgene capable of reducing the expression and/or the activity of the PARG encoding genes of the plants or plants cells, as described e.g. in WO 2004/090140.

3) a transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/ 002433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/ 030942, WO 2005/030941, WO 2005/095632, WO 2005/ 095617, WO 2005/095619, WO 2005/095618, WO 2005/ 123927, WO 2006/018319, WO 2006/103107, WO 2006/ 108702, WO 2007/009823, WO 00/22140, WO 2006/ 063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. No. 5,824,790, U.S. Pat. No. 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. No. 6,284,479, U.S. Pat. No. 5,712, 107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

The invention also provides a method for introducing a deletion at a predefined or preselected site in a (nuclear) genome of a transgenic plant cell comprising the steps of
a. inducing a double stranded DNA break at the predefined site; and
b. selecting a plant cell having a deletion at said predefined site;

wherein the predefined site is a nucleotide sequence different from a recognition site for a natural occurring meganuclease and is a nucleotide sequence commonly introduced as part of a transgene in a transgenic plant and wherein double stranded DNA break is induced by introduction of a non-naturally occurring single chain meganuclease or a pair of non-naturally occurring meganuclease monomeric units which recognizes or recognize together the predefined site and induces or induce the double stranded break.

It is also an embodiment of the invention to provide chimeric genes encoding re-designed meganucleases as herein described, wherein the chimeric gene comprise a plant expressible promoter operably linked to a DNA region encoding a protein comprising an amino acid sequence corresponding to the amino acid sequence of I-CreI as a scaffold comprising a S at position 32; R at position 33; Q at position 80; R at position 40; K at position 66; Y at position 68; S at position 70; Q at position 44; K at position 24; S at position 28 and E at position 30 or comprising R at position 70; Q at position 44; Q at position 26; K at position 28; N at position 30; S at position 32; C at position 33; Q at position 38; Q at position 80; M at position 40; C at position 79; and K at position 66, (positions with respect to the amino acid sequence of I-CreI, corresponding amino acid positions in redesigned meganucleases can be determined by alignment), such as the protein comprising the amino acid sequence of SEQ ID 3 or SEQ ID 4 or SEQ ID 5.

It will be appreciated that the means and methods of the invention may be used in any plant including corn, tobacco, cereal plants including wheat, oat, barley, rye, rice, turfgrass, sorghum, millet or sugarcane plants. The methods of the invention can also be applied to any plant (Angiospermae or Gymnospermae) including but not limited to cotton, canola, oilseed rape, soybean, vegetables, potatoes, *Lemna* spp., *Nicotiana* spp., *Arabidopsis*, alfalfa, barley, bean, corn, cotton, flax, pea, rape, rice, rye, safflower, sorghum, soybean, sunflower, tobacco, wheat, asparagus, beet and sugar beet, broccoli, cabbage, carrot, cauliflower, celery, cucumber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon.

It is also an object of the invention to provide plant cells and plants generated according to the methods of the invention. Gametes, seeds, embryos, either zygotic or somatic, progeny or hybrids of plants comprising the DNA insertion events, which are produced by traditional breeding methods, are also included within the scope of the present invention. Such plants may contain a heterologous or foreign DNA sequence inserted at or instead of a target sequence, and will only be different from their progenitor plants by the presence of this heterologous DNA or DNA sequence post exchange.

The plants obtained by the methods described herein may be further crossed by traditional breeding techniques with other plants to obtain progeny plants comprising the targeted DNA insertion events obtained according to the present invention.

The plants and seeds according to the invention may be further treated with a chemical compound, such as a chemical compound selected from the following lists:

Fruits/Vegetables Herbicides: Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam;

Fruits/Vegetables Insecticides: Aldicarb, *Bacillus thurengiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid;

Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin;

Cereals herbicides: 2.4-D, amidosulfuron, bromoxynil, carfentrazone-e, chlorotoluron, chlorsulfuron, clodinafop-p, clopyralid, dicamba, diclofop-m, diflufenican, fenoxaprop, florasulam, flucarbazone-na, flufenacet, flupyrsulfuron-m, fluroxypyr, flurtamone, glyphosate, iodosulfuron, ioxynil, isoproturon, mcpa, mesosulfuron, metsulfuron, pendimethalin, pinoxaden, propoxycarbazone, prosulfocarb, pyroxsulam, sulfosulfuron, thifensulfuron, tralkoxydim, triasulfuron, tribenuron, trifluralin, tritosulfuron;

Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin;

Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor;

Maize Herbicides: Atrazine, Alachlor, Bromoxynil, Acetochlor, Dicamba, Clopyralid, (S-)Dimethenamid, Glufosinate, Glyphosate, Isoxaflutole, (S-) Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon;

Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Tebupirimphos, Ethiprole, Cyazypyr, Thiacloprid, Acetamiprid, Dinetofuran, Avermectin;

Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin;

Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan;

Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor;

Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin;

Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron;

Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat;

Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor;

Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin;

Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-)Metolachlor, Metribuzin, Pendimethalin, Tepraloxydim, Glufosinate;

Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin;

Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin;

Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop;

Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran;

Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim;

Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad., Picoxystrobin, Prochloraz, Prothioconazole, Pyraclostrobin, Tebuconazole, Thiophanate-methyl, Trifloxystrobin, Vinclozolin;

Canola Insecticides: Carbofuran, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined may comprise additional DNA regions etc.

As used herein, "plant part" includes any plant organ or plant tissue, including but not limited to fruits, seeds, embryos, meristematic regions, callus tissue, leaves, roots, shoots, flowers, gametophytes, sporophytes, pollen, and microspores.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

The following non-limiting Examples describe the use of a re-designed meganuclease to modify plants at the site of a 3'gene 7 nucleotide sequence already present in the plant genome.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R.D.D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications and publications mentioned herein are hereby incorporated by reference, in their entireties, for all purposes.

Throughout the description and Examples, reference is made to the following sequences:

SEQ ID No. 1: nucleotide sequence of the recognition site of the re-designed meganucleases BAY 35/BAY36.

SEQ ID No. 2: nucleotide sequence of the 3' end of gene 7 *Agrobacterium* octopine type T-DNA as present e.g. in the target tobacco line (complement of "normal" orientation).

SEQ ID No. 3: nucleotide sequence of the T-DNA vector pCV176 expressing a pair of heterodimer meganucleases BAY 35 and BAY36.

SEQ ID No. 4: amino acid sequence of the meganuclease BAY35.

SEQ ID No. 5: amino acid sequence of the meganuclease BAY36.

SEQ ID No. 6: nucleotide sequence of the T-DNA vector pCV169 expressing a single chain meganuclease BAY 35-36.

SEQ ID No. 7: amino acid sequence of the single chain meganuclease BAY35/36, of which amino acids 1-12 comprise an SV20 nuclear localization signal.

SEQ ID No. 8: amino acid sequence of I-CreI natural variant.

EXAMPLES

All re-designed meganucleases described herein have been designed by Precision BioSciences Inc., 104 T.W. Alexander Drive, Research Triangle Park, N.C. 27713.

Example 1

Description of the T-DNA Vectors Encoding Re-Designed Meganucleases According to the Inventon Using conventional recombinant DNA techniques a chimeric gene encoding a single chain re-designed meganuclease recognizing the nucleotide sequence of SEQ ID No. 1 (scBAY35-36) comprising the following operably linked DNA fragments:
  a DNA region encoding the CaMV35S promoter (SEQ ID No 7 from nt position 691 to nt position 1223)
  a DNA region encoding the 5'UTR leader atsib (SEQ ID No 7 from nt position 1224 to nt position 1266)
  a DNA region comprising the 5' part of the BAY 35-36 sc coding region, operably linked to a SV40 NLS at the N-terminus (SEQ ID No 7 from nt position 1267 to 1602, such as the nucleotide sequence of SEQ ID No 7 from 1267 to 1605)
  a ST-LS1 intron (SEQ ID No 7 from nt position 1603 to 1795, such as the nucleotide sequence of SEQ ID No 7 from nt 1606 to 1794)
  a DNA region comprising the 3' part of the BAY 35-36 sc coding region (SEQ ID No 7 from nt position 1796 to 2544, such as the nucleotide sequence of SEQ ID No 7 from nt 1795 to 2541)
  a DNA region involved in 3' end transcription termination and polyadenylation from CaMV35S (SEQ ID No 7 from nt position 2545 to 2678).

The nucleotide sequence of the resulting plasmid pCV169 is represented in SEQ ID No. 6.

Also using conventional recombinant DNA techniques a chimeric gene encoding a pair of re-designed meganuclease monomers which as a heterodimer recognize the nucleotide sequence of SEQ ID No. 1 (hd BAY35-36) comprising the following operably linked DNA fragments:
  a DNA region encoding the CaMV35S promoter (SEQ ID No 6 from nt position 1516 to nt position 1933)
  a DNA region comprising the BAY 35 coding region, operably linked to a SV40 NLS at the N-terminus (SEQ ID No 6 from nt position 2004 to 2525, such as the nucleotide sequence of SEQ ID No 7 from nt 2004 to 2522)
  a DNA region involved in 3' end transcription termination and polyadenylation from nopaline synthase gene (SEQ ID No 6 from nt position 2530 to 2783)
  a DNA region encoding the CaMV35S promoter (SEQ ID No 6 from nt position 4397 to nt position 4814)
  a DNA region comprising the BAY 36 coding region, operably linked to a SV40 NLS at the N-terminus (SEQ ID No 6 from nt position 4885 to 5405, such as the nucleotide sequence of SEQ ID No 7 from nt 4885 to 5403)

a DNA region involved in 3' end transcription termination and polyadenylation from nopaline synthase gene (SEQ ID No 6 from nt position 5411 to 5664)

The nucleotide sequence of the resulting plasmid pCV176 is represented in SEQ ID No. 3.

Example 2

Description of the T-DNA Vectors Encoding Re-Designed Meganucleases According to the Invention In order to develop an assay for double stranded DNA break induced homology-mediated recombination, a tobacco transgenic plant line was isolated that contained a promoterless bar gene preceded by an I-SceI recognition site and the recognition site having the nucleotide sequence of SEQ ID No 1 (located in the 3' g7 region—see FIG. 1) integrated in the nuclear genome in single copy. Upon double stranded DNA break induction through delivery of an I-SceI endonuclease encoding plant expressible chimeric gene or the BAY35/36 sc or hd endonuclease, and co-delivery of repair DNA comprising a CaMV 35S promoter operably linked to the 5'end of the bar gene, the 35S promoter may be inserted through homology mediated targeted DNA insertion, resulting in a functional bar gene allowing resistance to phosphinotricin (PPT). The assay is schematically represented in FIG. 1.

The target locus was constructed by operably linking through conventional cloning techniques the following DNA regions a) a 3' end termination and polyadenylation signal from the nopaline synthetase gene
b) a promoter-less bar encoding DNA region
c) a DNA region comprising an I-SceI recognition site
d) a 3' end termination and polyadenylation signal from *A. tumefaciens* gene 7 (3'g7)
e) a plant expressible neomycin resistance gene comprising a nopaline synthetase promoter, a neomycine phosphotransferase gene, and a 3' ocs signal This DNA region was inserted in a T-DNA vector between the T-DNA borders. The T-DNA vector was designated pTTAM78.

The T-DNA vector was used directly to transform tobacco plants and a number of target lines were identified that contained a single copy of the target locus construct pTTAM78.

Example 3

Homology Based Targeted Insertion

The repair DNA pTTA82 is a T-DNA vector containing between the T-DNA borders the following operably linked DNA regions:

a) a DNA region encoding only the aminoterminal part of the bar gene
b) a CaMV 35S promoter region
c) a chimeric plant expressible neomycine resistance gene This repair DNA was co-delivered into tobacco protoplasts either with pCV78 (see Example 1 of WO 2005/049842) encoding I-SCeI or with pCV169 encoding scBAY35/36 or with pCV176 encoding the two monomeric units of hdBAY35/36. Delivery of the DNA was achieved by electroporation or by *Agrobacterium* transfection.

Phosphinotricin resistant events were selected and normalized as number of PPT resistant events per unit of initially co-cultivated protoplasts. The results are summarized in the Tables below.

TABLE 1

Agrobacterium mediated delivery of repair DNA in presence of either scBAY35/36 or I-SceI. Number of $PPT^R$ events/$2.5 \times 10^6$ co-cultivated protoplasts.

| scBAY35/36 | | I-SceI | |
|---|---|---|---|
| Plate number | $PPT^R$ | Plate number | $PPT^R$ |
| Experiment 1 | | | |
| 1 | 1 | 1 | 78 |
| 2 | 0 | 2 | 88 |
| 3 | 2 | 3 | 102 |
| 4 | 2 | 4 | 94 |
| 5 | 1 | 5 | 70 |
| 6 | 0 | 6 | 66 |
| Mean | 1 ± 0.9 | Mean | 83 ± 14 |
| Experiment 2 | | | |
| 1 | 0 | 1 | 85 |
| 2 | 2 | 2 | 101 |
| 3 | 1 | 3 | 98 |
| 4 | 1 | 4 | 80 |
| 5 | 5 | 5 | 105 |
| 6 | 8 | 6 | 95 |
| 7 | 6 | | |
| 8 | 6 | | |
| 9 | 5 | | |
| 10 | 11 | | |
| 11 | 11 | | |
| Mean | 5 ± 3.85 | Mean | 94 ± 9.6 |
| Experiment 3 | | | |
| 1 | 6 | 1 | 40 |
| 2 | 1 | 2 | 9 |
| 3 | 0 | 3 | 17 |
| 4 | 0 | 4 | 43 |
| 5 | 1 | 5 | 20 |
| 6 | 1 | 6 | 53 |
| 7 | 0 | | |
| 8 | 4 | | |
| 9 | 1 | | |
| 10 | 1 | | |
| 11 | 1 | | |
| Mean | 1.45 ± 1.9 | Mean | 30 ± 17.4 |

A number of phosphinotricin resistant events were also characterized at the molecular level by Southern hybridization after digestion of genomic DNA with PstI using as probe either 3'nos or CaMV35S probes. In the case of repair of the bar coding region and insertion of the CaMV35S promoter via homologous recombination, both probes should reveal a fragment of about 2362 bp. If the target locus has not been repaired, a PstI fragment of about 1735 bp is expected. All analyzed events (about 20) revealed the same 2362 bp fragment after hybridization with both probes, indicating insertion of the 35S and 5' region of the bar coding through homologous recombination.

From these experiments it may thus be concluded that scBAY35/36 exhibits cleavage activity at the preselected site, as observed from the HR-mediated target sequence insertion at a frequency of about 1 to 5% when compared with the cleavage induced by I-SceI.

TABLE 2

Electroporation mediated delivery of repair DNA in presence of either scBAY35/36, hdBAY35/36 or I-SceI. Number of PPT$^R$ events/1 × 10$^6$ electroporated protoplasts.

| hdBAY35/36 | | scBAY35/36 | | I-SceI | |
|---|---|---|---|---|---|
| Cuvette Nr. | PPT$^R$ | Cuvette Nr. | PPT$^R$ | Cuvette Nr. | PPT$^R$ |
| Experiment 1 | | | | | |
| 1 | 1 | | | 1 | 25 |
| 2 | 0 | | | 2 | 29 |
| 3 | 0 | | | 3 | 16 |
| 4 | 1 | | | 4 | 21 |
| | | | | 5 | 45 |
| | | | | 6 | 22 |
| Mean | 0.5 ± 0.6 | | | Mean | 26.3 ± 10.1 |
| Experiment 2 | | | | | |
| 1 | 1 | 1 | 1 | 1 | 50 |
| 2 | 1 | 2 | 0 | 2 | 48 |
| 3 | 1 | 3 | 1 | 3 | 64 |
| 4 | 0 | 4 | 1 | 4 | 49 |
| 5 | 0 | 5 | 1 | | |
| 6 | 1 | 6 | 2 | | |
| Mean | 0.7 ± 0.5 | Mean | 1 ± 0.6 | Mean | 52.8 ± 7.5 |

From these experiments it may thus be concluded that both hdBAY35/36 and scBAY35/36 exhibits cleavage activity at the preselected site, as observed from the HR-mediated target sequence insertion at a frequency of about 2% when compared with the cleavage induced by I-SceI.

The invention claimed is:

1. A method for introducing a foreign DNA molecule at a predefined site in a genome of a plant cell comprising the steps of
   a. inducing a double stranded DNA break at said predefined site;
   b. introducing said foreign DNA molecule in said plant cell; and
   c. selecting a plant cell wherein said foreign DNA is introduced at said predefined site;
   characterized in that said predefined site is comprised within SEQ ID NO. 2 and that said double stranded DNA break is induced by introduction of a single chain meganuclease or a pair of meganucleases which recognizes or recognize in concert said predefined site and induces or induce said double stranded break.

2. A method for introducing a foreign DNA molecule at a predefined site in a genome of a plant cell comprising the steps of
   a. inducing a double stranded DNA break at said predefined site;
   b. introducing said foreign DNA molecule in said plant cell; and
   c. selecting a plant cell wherein said foreign DNA is introduced at said predefined site;
   characterized in that said predefined site comprises the nucleotide sequence of SEQ ID No. 1 and that said double stranded DNA break is induced by introduction of a single chain meganuclease or a pair of meganucleases which recognizes or recognize in concert said predefined site and induces or induce said double stranded break.

3. The method according to any one of claims 1 or 2, wherein said meganuclease or said pair of meganucleases is/are derived from I-CreI and wherein the following amino acids are present in meganuclease unit 1:
   a. S at position 32;
   b. R at position 33;
   c. Q at position 80;
   d. R at position 40;
   e. K at position 66;
   f. Y at position 68;
   g. S at position 70;
   h. Q at position 44;
   i. K at position 24;
   j. S at position 28;
   k. E at position 30;
   and wherein the following amino acids are present in meganuclease unit 2:
   L. R at position 70;
   m. Q at position 44;
   n. Q at position 26;
   o. K at position 28;
   p. N at position 30;
   q. S at position 32;
   r. C at position 33;
   s. Q at position 38;
   t. Q at position 80;
   u. M at position 40;
   v. C at position 79;
   w. K at position 66;
   x. R at position 77;
   y. Y at position 68.

4. The method according to any one of claims 1 or 2, wherein said pair of meganucleases obligatory forms heterodimers or wherein said meganuclease is a single chain meganuclease comprising two domains derived from I-CreI covalently connected by a linker.

5. The method according to any one of claims 1 or 2, wherein said pair of meganucleases comprises the amino acid sequence of SEQ ID No. 4 and SEQ ID No. 5, respectively, or wherein said pair of meganucleases is encoded by a nucleic acid comprising the nucleotide sequence of SEQ ID No. 3 from nucleotide position 2004 to nucleotide position 2525 or to 2522, or the nucleotide sequence of SEQ ID No. 3 from nucleotide position 4885 to nucleotide position 5405 or to 5403, or wherein said single chain meganuclease comprises the amino acid sequence of SEQ ID No. 7 or said single chain meganuclease comprises an amino acid sequence comprising the amino acid sequence of SEQ ID No. 7 from position 1 to 167 and from position 206 to 362, or wherein said single chain meganuclease is encoded by a nucleotide sequence comprising the nucleotide sequence of SEQ ID No. 6 from position 1267 to position 1602 or to 1605 and from position 1796 or from 1795 to position 2544 or to 2541, or said single chain meganuclease is encoded by a nucleotide sequence comprising the nucleotide sequence of SED ID No. 6 from position 1267 to 1605 and from 1796 to 1956 and from 2071 to 2541.

6. The method according to any one of claims 1 or 2, wherein said foreign DNA is comprised within a repair DNA, said repair DNA comprising at least one flanking nucleotide sequence homologous to the upstream or downstream sequence of the nucleotide sequence of SEQ ID No. 1.

7. The method according to any one of claims 1 or 2, wherein said meganuclease or said pair of meganucleases is expressed from a chimeric gene or a pair of chimeric genes, each comprising a plant expressible promoter operably linked to a coding region encoding said meganuclease or one of said pair of meganucleases, and further operationally linked to a DNA region involved in transcription termination and polyadenylation functional in a plant cell.

8. The method according to any one of claims 1 or 2, wherein said foreign DNA comprises a selectable marker gene and/or a plant expressible gene of interest, said plant expressible gene of interest optionally being selected from the group of a herbicide tolerance gene, an insect resistance gene, a disease resistance gene, an abiotic stress resistance gene, an enzyme involved in oil biosynthesis, carbohydrate biosynthesis, an enzyme involved in fiber strength or fiber length, an enzyme involved in biosynthesis of secondary metabolites.

9. The method according to any one of the preceding claims 1 or 2, wherein said plant cell is further regenerated into a plant.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial
<220> FEATURE:
<223> OTHER INFORMATION: Recognition site for re-designed meganuclease
      BAY35/36

<400> SEQUENCE: 1
cgggatcttg aaagaaatat ag                                                22

<210> SEQ ID NO 2
<211> LENGTH: 327
<212> TYPE: DNA
<213> ORGANISM: Artificial
<220> FEATURE:
<223> OTHER INFORMATION: 3' end of Agrobacterium octopine T-DNA type
      gene 7

<400> SEQUENCE: 2
cgggatcttg aaagaaatat agtttaaata tttattgata aaataacaag tcaggtatta      60
tagtccaagc aaaaacataa atttattgat gcaagtttaa attcagaaat atttcaataa     120
ctgattatat cagctggtac attgccgtag atgaaagact gagtgcgata ttatgtgtaa     180
tacataaatt gatgatatag ctagcttagg cgcgccatag atcccgtcaa ttctcactca     240
ttaggcaccc caggctttac actttatgct tccggctcgt ataatgtgtg gaattgtgag     300
cggataacaa tttcacacag gaaacag                                         327

<210> SEQ ID NO 3
<211> LENGTH: 6234
<212> TYPE: DNA
<213> ORGANISM: Artificial
<220> FEATURE:
<223> OTHER INFORMATION: nucleotide sequence of T-DNA vector pCV176
      expressing a pair of heterodimer meganucleases BAY35 and 36.
<220> FEATURE:
<221> NAME/KEY: CDS
<222> LOCATION: (2004)..(2522)
<220> FEATURE:
<221> NAME/KEY: CDS
<222> LOCATION: (4885)..(5403)

<400> SEQUENCE: 3

```
gacgaaaggg cctcgtgata cgcctatttt tataggttaa tgtcatgata ataatggttt       60
cttagacgtc aggtggcact tttcggggaa atgtgcgcgg aacccctatt tgtttatttt      120
tctaaataca ttcaaatatg tatccgctca tgagacaata accctgataa atgcttcaat      180
aatattgaaa aggaagagt atgagtattc aacatttccg tgtcgccctt attccctttt       240
ttgcggcatt ttgccttcct gttttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgctttttttg cacaacatgg     660 gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc atttttaatt taaaaggatc taggtgaaga    1140
tcctttttgc tagcgagagg cggtttgcgt attggctaga gcagcttgcc aacatggtgg    1200
agcacgacac tctcgtctac tccaagaata tcaaagatac agtctcagaa gaccaaaggg    1260
ctattgagac ttttcaacaa agggtaatat cgggaaacct cctcggattc cattgcccag    1320
ctatctgtca cttcatcaaa aggacagtag aaaaggaagg tggcacctac aaatgccatc    1380
attgcgataa aggaaaggct atcgttcaag atgcctctgc cgacagtggt cccaaagatg    1440
gacccccacc cacgaggagc atcgtggaaa aagaagacgt tccaaccacg tcttcaaagc    1500
aagtggattg atgtgaacat ggtggagcac gacactctcg tctactccaa gaatatcaaa    1560
gatacagtct cagaagacca aagggctatt gagactttc aacaagggt aatatcggga    1620 aacctcctcg gattccattg cccagctatc tgtcacttca tcaaaggac agtagaaaag    1680 gaaggtggca cctacaaatg ccatcattgc gataaaggaa aggctatcgt tcaagatgcc    1740
tctgccgaca gtggtcccaa agatggaccc ccacccacga ggagcatcgt ggaaaaagaa    1800
gacgttccaa ccacgtcttc aaagcaagtg gattgatgtg atatctccac tgacgtaagg    1860
gatgacgcac aatcccacta ccttcgcaa gaccccttcct ctatataagg aagttcattt    1920
catttggaga ggacacgctg aaatcaccag tctctctcta caaatctatc tctctcgagc    1980
```
tttcgcagat ctgtcgaacc acc atg gca ccg aag aag aag cgc aag gtg cat    2033
                                     Met Ala Pro Lys Lys Lys Arg Lys Val His
                                     1         5               10 atg aac acc aag tac aac aag aag ttc ctg ctc tac ctg gcg ggc ttc    2081
Met Asn Thr Lys Tyr Asn Lys Lys Phe Leu Leu Tyr Leu Ala Gly Phe
               15                  20               25 gtg gac ggg gac ggc tcc atc aag gcc cag atc tcc ccg gag cag tcc    2129
Val Asp Gly Asp Gly Ser Ile Lys Ala Gln Ile Ser Pro Glu Gln Ser
             30                  35               40

| | | | | | | | | | | | | | | | | |
|---|---|---|---|---|---|---|---|---|---|---|---|---|---|---|---|---|
| cgc | aag | ttc | aag | cat | cgc | ctg | cgc | ctc | acc | ttc | cag | gtc | acg | cag | aag | 2177 |
| Arg | Lys | Phe | Lys | His | Arg | Leu | Arg | Leu | Thr | Phe | Gln | Val | Thr | Gln | Lys | |
| | 45 | | | | 50 | | | | | 55 | | | | | | |
| aca | cag | cgc | cgt | tgg | ttc | ctc | gac | aag | ctg | gtg | gac | aag | atc | ggg | gtg | 2225 |
| Thr | Gln | Arg | Arg | Trp | Phe | Leu | Asp | Lys | Leu | Val | Asp | Lys | Ile | Gly | Val | |
| 60 | | | | | 65 | | | | | 70 | | | | | | |
| ggc | aag | gtg | tac | gac | tcc | ggc | agc | gtc | tcc | gac | tac | atc | ctg | tcc | cag | 2273 |
| Gly | Lys | Val | Tyr | Asp | Ser | Gly | Ser | Val | Ser | Asp | Tyr | Ile | Leu | Ser | Gln | |
| 75 | | | | | 80 | | | | | 85 | | | | | | 90 |
| atc | aag | cct | ctg | cac | aac | ttc | ctg | acc | cag | ctc | cag | ccc | ttc | ctg | aag | 2321 |
| Ile | Lys | Pro | Leu | His | Asn | Phe | Leu | Thr | Gln | Leu | Gln | Pro | Phe | Leu | Lys | |
| | | | | | 95 | | | | | 100 | | | | | 105 | |
| ctc | aag | cag | aag | cag | gcc | aac | ctc | gtg | ctg | aag | atc | atc | gag | cag | ctg | 2369 |
| Leu | Lys | Gln | Lys | Gln | Ala | Asn | Leu | Val | Leu | Lys | Ile | Ile | Glu | Gln | Leu | |
| | | | 110 | | | | | 115 | | | | | 120 | | | |
| ccc | tcc | gcc | aag | gaa | tcc | ccg | gac | aag | ttc | ctg | gag | gtg | tgc | acc | tgg | 2417 |
| Pro | Ser | Ala | Lys | Glu | Ser | Pro | Asp | Lys | Phe | Leu | Glu | Val | Cys | Thr | Trp | |
| | | | 125 | | | | | 130 | | | | | 135 | | | |
| gtg | gac | cag | atc | gcc | gct | ctg | aac | gac | tcc | aag | acc | cgc | aag | acc | act | 2465 |
| Val | Asp | Gln | Ile | Ala | Ala | Leu | Asn | Asp | Ser | Lys | Thr | Arg | Lys | Thr | Thr | |
| | 140 | | | | | 145 | | | | | 150 | | | | | |
| tca | gag | acc | gtc | cgc | gcc | gtt | cta | gac | agt | ctc | tcc | gag | aag | aag | aag | 2513 |
| Ser | Glu | Thr | Val | Arg | Ala | Val | Leu | Asp | Ser | Leu | Ser | Glu | Lys | Lys | Lys | |
| 155 | | | | | 160 | | | | | 165 | | | | | 170 | |
| tcg | tcc | ccc | tagcatgccg | ttcaaacatt | tggcaataaa | gtttcttaag | | | | | | | | | | 2562 |
| Ser | Ser | Pro | | | | | | | | | | | | | | |

| | |
|---|---|
| attgaatcct gttgccggtc ttgcgatgat tatcatataa tttctgttga attacgttaa | 2622 |
| gcatgtaata attaacatgt aatgcatgac gttatttatg agatgggttt ttatgattag | 2682 |
| agtcccgcaa ttatacattt aatacgcgat agaaaacaaa atatagcgcg caaactagga | 2742 |
| taaattatcg cgcgcggtgt catctatgtt actagatcgg gcccgggaat aaaatatctt | 2802 |
| tattttcatt acatctgtgt gttggttttt tgtgtgaatc gatagtacta acatacgctc | 2862 |
| tccatcaaaa caaaacgaaa caaaacaaac tagcaaaata ggctgtcccc agtgcaagtg | 2922 |
| caggtgccag aacatttctc tgctagcctc atgaccaaaa tcccttaacg tgagttttcg | 2982 |
| ttccactgag cgtcagaccc cgtagaaaag atcaaaggat cttcttgaga tccttttttt | 3042 |
| ctgcgcgtaa tctgctgctt gcaaacaaaa aaaccaccgc taccagcggt ggtttgtttg | 3102 |
| ccggatcaag agctaccaac tcttttttccg aaggtaactg gcttcagcag agcgcagata | 3162 |
| ccaaatactg ttcttctagt gtagccgtag ttaggccacc acttcaagaa ctctgtagca | 3222 |
| ccgcctacat acctcgctct gctaatcctg ttaccagtgg ctgctgccag tggcgataag | 3282 |
| tcgtgtctta ccgggttgga ctcaagacga tagttaccgg ataaggcgca gcggtcgggc | 3342 |
| tgaacggggg gttcgtgcac acagcccagc ttggagcgaa cgacctacac cgaactgaga | 3402 |
| tacctacagc gtgagctatg agaaagcgcc acgcttcccg aagggagaaa ggcggacagg | 3462 |
| tatccggtaa gcggcaggt cggaacagga gagcgcacga gggagcttcc agggggaaac | 3522 |
| gcctggtatc tttatagtcc tgtcgggttt cgccacctct gacttgagcg tcgatttttg | 3582 |
| tgatgctcgt cagggggcg gagcctatgg aaaaacgcca gcaacgcggc ctttttacgg | 3642 |
| ttcctggcct tttgctggcc ttttgctcac atgttctttc ctgcgttatc ccctgattct | 3702 |
| gtggataacc gtattaccgc ctttgagtga gctgataccg ctcgccgcag ccgaacgacc | 3762 |
| gagcgcagcg agtcagtgag cgaggaagcg gaagagcgcc caatacgcaa accgcctctc | 3822 |
| cccgcgcgtt ggccgattca ttaatgcagc tggcacgaca ggtttcccga ctggaaagcg | 3882 |

```
ggcagtgagc gcaacgcaat taatgtgagt tagctcactc attaggcacc ccaggcttta    3942
cactttatgc ttccggctcg tatgttgtgt ggaattgtga gcggataaca atttcacaca    4002
ggaaacagct atgaccatga ttacgccaag cttgagaggc ggtttgcgta ttggctagag    4062
cagcttgcca acatggtgga gcacgacact ctcgtctact ccaagaatat caaagataca    4122
gtctcagaag accaaagggc tattgagact tttcaacaaa gggtaatatc gggaaacctc    4182
ctcggattcc attgcccagc tatctgtcac ttcatcaaaa ggacagtaga aaggaaggt    4242 ggcacctaca aatgccatca ttgcgataaa ggaaaggcta tcgttcaaga tgcctctgcc    4302
gacagtggtc ccaaagatgg accccaccc acgaggagca tcgtgaaaaa agaagacgtt    4362
ccaaccacgt cttcaaagca gtggattga tgtgaacatg gtggagcacg acactctcgt    4422
ctactccaag aatatcaaag atacagtctc agaagaccaa agggctattg agactttca    4482 acaaaggta atatcgggaa acctcctcgg attccattgc ccagctatct gtcacttcat    4542
caaaaggaca gtagaaaagg aaggtggcac ctacaaatgc catcattgcg ataaaggaaa    4602
ggctatcgtt caagatgcct ctgccgacag tggtcccaaa gatggacccc cacccacgag    4662
gagcatcgtg aaaaagaag acgttccaac cacgtcttca aagcaagtgg attgatgtga    4722
tatctccact gacgtaaggg atgacgcaca atcccactat ccttcgcaag acccttcctc    4782
tatataagga agttcatttc atttggagag gacacgctga aatcaccagt ctctctctac    4842
aaatctatct ctctcgagct ttcgcagatc tgtcgaacca cc atg gca ccg aag       4896
                                              Met Ala Pro Lys
                                                           175 aag aag cgc aag gtg cat atg aac acc aag tac aac gag gag ttc ctg      4944
Lys Lys Arg Lys Val His Met Asn Thr Lys Tyr Asn Glu Glu Phe Leu
        180                 185                 190 ctc tac ctg gcg ggc ttc gtg gac ggg gac ggc tcc atc atc gcc cag      4992
Leu Tyr Leu Ala Gly Phe Val Asp Gly Asp Gly Ser Ile Ile Ala Gln
        195                 200                 205 atc aag ccg aac cag tcc tgc aag ttc aag cat cag ctg atg ctc acc      5040
Ile Lys Pro Asn Gln Ser Cys Lys Phe Lys His Gln Leu Met Leu Thr
210                 215                 220                 225 ttc cag gtc acg cag aag aca cag cgc cgt tgg ttc ctc gac gag ctg      5088
Phe Gln Val Thr Gln Lys Thr Gln Arg Arg Trp Phe Leu Asp Glu Leu
            230                 235                 240 gtg gac gag atc ggg gtg ggc aag gtg tac gac cgc ggc agc gtc tcc      5136
Val Asp Glu Ile Gly Val Gly Lys Val Tyr Asp Arg Gly Ser Val Ser
        245                 250                 255 gac tac cgc ctg tgc cag atc aag cct ctg cac aac ttc ctc acc cag      5184
Asp Tyr Arg Leu Cys Gln Ile Lys Pro Leu His Asn Phe Leu Thr Gln
        260                 265                 270 ctc cag ccc ttc ctg gag ctc aag cag aag cag gcc aac ctc gtg ctg      5232
Leu Gln Pro Phe Leu Glu Leu Lys Gln Lys Gln Ala Asn Leu Val Leu
        275                 280                 285 aag atc atc gag cag ctg ccc tcc gcc aag gaa tcc ccg gac aag ttc      5280
Lys Ile Ile Glu Gln Leu Pro Ser Ala Lys Glu Ser Pro Asp Lys Phe
290                 295                 300                 305 ctg gag gtg tgc acc tgg gtg gac cag atc gcc gct ctg aac gac tcc      5328
Leu Glu Val Cys Thr Trp Val Asp Gln Ile Ala Ala Leu Asn Asp Ser
                310                 315                 320 aag acc cgc aag acc act tcc gag acc gtc cgc gcc gtt cta gac agt      5376
Lys Thr Arg Lys Thr Thr Ser Glu Thr Val Arg Ala Val Leu Asp Ser
        325                 330                 335 ctc tcc gag aag aag aag tcg tcc ccc tagcatgccg ttcaaacatt            5423
Leu Ser Glu Lys Lys Lys Ser Ser Pro
```

```
                    340                 345
tggcaataaa gtttcttaag attgaatcct gttgccggtc ttgcgatgat tatcatataa    5483
tttctgttga attacgttaa gcatgtaata attaacatgt aatgcatgac gttatttatg    5543
agatgggttt ttatgattag agtcccgcaa ttatacattt aatacgcgat agaaaacaaa    5603
atatagcgcg caaactagga taaattatcg cgcgcggtgt catctatgtt actagatcgg    5663
gcccgggaat aaaatatctt tattttcatt acatctgtgt gttggttttt tgtgtgaatc    5723
gatagtacta acatacgctc tccatcaaaa caaaacgaaa caaaacaaac tagcaaaata    5783
ggctgtcccc agtgcaagtg caggtgccag aacatttcgg taccgagctc gaattcactg    5843
gccgtcgttt tacaacgtcg tgactgggaa accctggcg ttacccaact taatcgcctt    5903
gcagcacatc cccctttcgc cagctggcgt aatagcgaag aggcccgcac cgatcgccct    5963
tcccaacagt tgcgcagcct gaatggcgaa tggcgcctga tgcggtattt tctccttacg    6023
catctgtgcg gtatttcaca ccgcatatgg tgcactctca gtacaatctg ctctgatgcc    6083
gcatagttaa gccagccccg acacccgcca acacccgctg acgcgccctg acgggcttgt    6143
ctgctcccgg catccgctta cagacaagct gtgaccgtct ccgggagctg catgtgtcag    6203
aggttttcac cgtcatcacc gaaacgcgcg a                                   6234
```

<210> SEQ ID NO 4
<211> LENGTH: 173
<212> TYPE: PRT
<213> ORGANISM: Artificial
<220> FEATURE:
<223> OTHER INFORMATION: Synthetic Construct

<400> SEQUENCE: 4

```
Met Ala Pro Lys Lys Arg Lys Val His Met Asn Thr Lys Tyr Asn
1               5                   10                  15

Lys Lys Phe Leu Leu Tyr Leu Ala Gly Phe Val Asp Gly Asp Gly Ser
            20                  25                  30

Ile Lys Ala Gln Ile Ser Pro Glu Gln Ser Arg Lys Phe Lys His Arg
        35                  40                  45

Leu Arg Leu Thr Phe Gln Val Thr Gln Lys Thr Gln Arg Arg Trp Phe
    50                  55                  60

Leu Asp Lys Leu Val Asp Lys Ile Gly Val Gly Lys Val Tyr Asp Ser
65                  70                  75                  80

Gly Ser Val Ser Asp Tyr Ile Leu Ser Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Ser Glu Lys Lys Lys Ser Ser Pro
                165                 170
```

<210> SEQ ID NO 5
<211> LENGTH: 173
<212> TYPE: PRT
<213> ORGANISM: Artificial
<220> FEATURE:

<223> OTHER INFORMATION: Synthetic Construct

<400> SEQUENCE: 5

```
Met Ala Pro Lys Lys Lys Arg Lys Val His Met Asn Thr Lys Tyr Asn
1               5                   10                  15

Glu Glu Phe Leu Leu Tyr Leu Ala Gly Phe Val Asp Gly Asp Gly Ser
            20                  25                  30

Ile Ile Ala Gln Ile Lys Pro Asn Gln Ser Cys Lys Phe Lys His Gln
        35                  40                  45

Leu Met Leu Thr Phe Gln Val Thr Gln Lys Thr Gln Arg Arg Trp Phe
50                  55                  60

Leu Asp Glu Leu Val Asp Glu Ile Gly Val Gly Lys Val Tyr Asp Arg
65                  70                  75                  80

Gly Ser Val Ser Asp Tyr Arg Leu Cys Gln Ile Lys Pro Leu His Asn
                85                  90                  95

Phe Leu Thr Gln Leu Gln Pro Phe Leu Glu Leu Lys Gln Lys Gln Ala
            100                 105                 110

Asn Leu Val Leu Lys Ile Ile Glu Gln Leu Pro Ser Ala Lys Glu Ser
            115                 120                 125

Pro Asp Lys Phe Leu Glu Val Cys Thr Trp Val Asp Gln Ile Ala Ala
        130                 135                 140

Leu Asn Asp Ser Lys Thr Arg Lys Thr Thr Ser Glu Thr Val Arg Ala
145                 150                 155                 160

Val Leu Asp Ser Leu Ser Glu Lys Lys Ser Ser Pro
                165                 170
```

<210> SEQ ID NO 6
<211> LENGTH: 4925
<212> TYPE: DNA
<213> ORGANISM: Artificial
<220> FEATURE:
<223> OTHER INFORMATION: Nucleotide sequence of a T-DNA vector
      expressing a single chain meganuclease BAY35-36.
<220> FEATURE:
<221> NAME/KEY: CDS
<222> LOCATION: (1267)..(1605)
<220> FEATURE:
<221> NAME/KEY: CDS
<222> LOCATION: (1795)..(2541)

<400> SEQUENCE: 6

| | | |
|---|---|---|
| ctaaattgta agcgttaata ttttgttaaa attcgcgtta aattttgtt aaatcagctc | 60 |
| attttttaac caataggccg aaatcggcaa atcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta gggcgaat tgggtacggc | 660 |
| cgtcaaggcc aagcttcccc cttaggatcc accatacatg gagtcaaaaa ttcagatcga | 720 |
| ggatctaaca gaactcgccg tgaagactgg cgaacagttc atacagagtc ttttacgact | 780 |

```
caatgacaag aagaaaatct tcgtcaacat ggtggagcac gacactctcg tctactccaa    840
gaatatcaaa gatacagtct cagaagacca aagggctatt gagacttttc aacaaagggt    900
aatatcggga aacctcctcg gattccattg cccagctatc tgtcacttca tcaaaaggac    960
agtagaaaag gaaggtggca cctacaaatg ccatcattgc gataaaggaa aggctatcgt   1020
tcaagatgcc tctgccgaca gtggtcccaa agatggaccc ccacccacga ggagcatcgt   1080
ggaaaaagaa gacgttccaa ccacgtcttc aaagcaagtg gattgatgtg atatctccac   1140
tgacgtaagg gatgacgcac aatcccacta tccttcgcaa gacccttcct ctatataagg   1200
aagttcattt catttggaga ggactcgaga attaagcaaa agaagaagaa gaagaagtcc   1260
```

| | | | | | | | | | | | | |
|---|---|---|---|---|---|---|---|---|---|---|---|---|
| aaaacc atg | gct | aaa | cct | ccc | aag | aaa | aag | cgc | aaa | gtg | cat atg aat | 1308 |
| Met | Ala | Lys | Pro | Pro | Lys | Lys | Lys | Arg | Lys | Val | His Met Asn | |
| 1 | | | 5 | | | | | 10 | | | | |

| act | aag | tac | aat | aag | gaa | ttt | ctc | ctt | tac | tta | gct | ggt | ttc | gtg | gat | 1356 |
|---|---|---|---|---|---|---|---|---|---|---|---|---|---|---|---|---|
| Thr | Lys | Tyr | Asn | Lys | Glu | Phe | Leu | Leu | Tyr | Leu | Ala | Gly | Phe | Val | Asp | |
| 15 | | | | 20 | | | | | 25 | | | | | 30 | | |

| ggc | gat | gga | tct | atc | ata | gct | cag | att | aaa | cca | aat | caa | tca | tgc | aag | 1404 |
|---|---|---|---|---|---|---|---|---|---|---|---|---|---|---|---|---|
| Gly | Asp | Gly | Ser | Ile | Ile | Ala | Gln | Ile | Lys | Pro | Asn | Gln | Ser | Cys | Lys | |
| | | | 35 | | | | | 40 | | | | | 45 | | | |

| ttc | aag | cac | caa | ctg | atg | ttg | acc | ttc | cag | gta | act | cag | aaa | acc | caa | 1452 |
|---|---|---|---|---|---|---|---|---|---|---|---|---|---|---|---|---|
| Phe | Lys | His | Gln | Leu | Met | Leu | Thr | Phe | Gln | Val | Thr | Gln | Lys | Thr | Gln | |
| | | | | 50 | | | | | 55 | | | | | 60 | | |

| agg | aga | tgg | ttc | tta | gat | aaa | ctt | gtc | gat | gaa | atc | ggc | gta | gga | aaa | 1500 |
|---|---|---|---|---|---|---|---|---|---|---|---|---|---|---|---|---|
| Arg | Arg | Trp | Phe | Leu | Asp | Lys | Leu | Val | Asp | Glu | Ile | Gly | Val | Gly | Lys | |
| | 65 | | | | | 70 | | | | | 75 | | | | | |

| gtg | tac | gat | agg | gga | tct | gtt | tcc | gac | tat | cga | ctt | tgt | caa | atc | aag | 1548 |
|---|---|---|---|---|---|---|---|---|---|---|---|---|---|---|---|---|
| Val | Tyr | Asp | Arg | Gly | Ser | Val | Ser | Asp | Tyr | Arg | Leu | Cys | Gln | Ile | Lys | |
| 80 | | | | | 85 | | | | | 90 | | | | | | |

| cct | ctt | cat | aat | ttt | ctc | act | cag | cta | cag | cca | ttt | cta | aag | ttg | aaa | 1596 |
|---|---|---|---|---|---|---|---|---|---|---|---|---|---|---|---|---|
| Pro | Leu | His | Asn | Phe | Leu | Thr | Gln | Leu | Gln | Pro | Phe | Leu | Lys | Leu | Lys | |
| 95 | | | | 100 | | | | | 105 | | | | | 110 | | |

| cag | aag | cag | gtaagtttct gcttctacct ttgatatata tataataatt | 1645 |
|---|---|---|---|---|
| Gln | Lys | Gln | | |

```
atcattaatt agtagtaata taatatttca aatattttt tcaaaataaa agaatgtagt    1705
atatagcaat tgcttttctg tagtttataa gtgtgtatat tttaatttat aacttttcta   1765
```

| atatatgacc | aaaacatggt | gatgtgcag | gca | aac | ttg | gtt | ctc | aag | atc | ata | 1818 |
|---|---|---|---|---|---|---|---|---|---|---|---|
| | | | Ala | Asn | Leu | Val | Leu | Lys | Ile | Ile | |
| | | | | | 115 | | | | | 120 | |

| gag | cag | tta | cca | tct | gca | aaa | gaa | agt | ccc | gac | aag | ttt | ctt | gag | gtt | 1866 |
|---|---|---|---|---|---|---|---|---|---|---|---|---|---|---|---|---|
| Glu | Gln | Leu | Pro | Ser | Ala | Lys | Glu | Ser | Pro | Asp | Lys | Phe | Leu | Glu | Val | |
| | | | 125 | | | | | 130 | | | | | 135 | | | |

| tgc | aca | tgg | gtt | gac | caa | atc | gca | gct | ttg | aat | gac | tcc | aaa | act | agg | 1914 |
|---|---|---|---|---|---|---|---|---|---|---|---|---|---|---|---|---|
| Cys | Thr | Trp | Val | Asp | Gln | Ile | Ala | Ala | Leu | Asn | Asp | Ser | Lys | Thr | Arg | |
| | | 140 | | | | | 145 | | | | | 150 | | | | |

| aaa | aca | act | tct | gag | act | gta | aga | gcc | gtc | tta | gac | tca | tta | cct | ggt | 1962 |
|---|---|---|---|---|---|---|---|---|---|---|---|---|---|---|---|---|
| Lys | Thr | Thr | Ser | Glu | Thr | Val | Arg | Ala | Val | Leu | Asp | Ser | Leu | Pro | Gly | |
| | | 155 | | | | | 160 | | | | | 165 | | | | |

| agc | gtc | ggt | ggg | tta | tca | cct | agt | caa | gct | agc | tct | gct | gca | tca | agc | 2010 |
|---|---|---|---|---|---|---|---|---|---|---|---|---|---|---|---|---|
| Ser | Val | Gly | Gly | Leu | Ser | Pro | Ser | Gln | Ala | Ser | Ser | Ala | Ala | Ser | Ser | |
| 170 | | | | | 175 | | | | | 180 | | | | | 185 | |

| gcc | agt | agc | tca | cca | ggt | agt | gga | atc | agt | gaa | gcc | ctt | aga | gca | ggg | 2058 |
|---|---|---|---|---|---|---|---|---|---|---|---|---|---|---|---|---|
| Ala | Ser | Ser | Ser | Pro | Gly | Ser | Gly | Ile | Ser | Glu | Ala | Leu | Arg | Ala | Gly | |
| | | | | 190 | | | | | 195 | | | | | 200 | | |

| gca | act | aag | tct | aag | gaa | ttc | ctc | ctt | tat | cta | gcc | ggt | ttt | gtg | gat | 2106 |
|---|---|---|---|---|---|---|---|---|---|---|---|---|---|---|---|---|
| Ala | Thr | Lys | Ser | Lys | Glu | Phe | Leu | Leu | Tyr | Leu | Ala | Gly | Phe | Val | Asp | |
| | | 205 | | | | | 210 | | | | | 215 | | | | |

```
ggt gat ggc tca att aaa gct cag ata tca cca gaa cag tct cga aag     2154
Gly Asp Gly Ser Ile Lys Ala Gln Ile Ser Pro Glu Gln Ser Arg Lys
        220                 225                 230 ttt aag cat aga ttg aga ttg act ttt caa gtg aca caa aag act cag     2202
Phe Lys His Arg Leu Arg Leu Thr Phe Gln Val Thr Gln Lys Thr Gln
    235                 240                 245 cgt agg tgg ttt ctg gac aaa ctg gtc gat gag att gga gtt ggg aaa     2250
Arg Arg Trp Phe Leu Asp Lys Leu Val Asp Glu Ile Gly Val Gly Lys
250                 255                 260                 265 gtt tat gac tcc gga tca gtt tcc gat tac ata ctg tct cag att aaa     2298
Val Tyr Asp Ser Gly Ser Val Ser Asp Tyr Ile Leu Ser Gln Ile Lys
                270                 275                 280 cca ctt cac aac ttc ctt aca caa ttg caa cct ttc ctc aag ttg aag     2346
Pro Leu His Asn Phe Leu Thr Gln Leu Gln Pro Phe Leu Lys Leu Lys
            285                 290                 295 caa aaa caa gca aac ctt gtt ctg aag ata att gag caa ctc cca tct     2394
Gln Lys Gln Ala Asn Leu Val Leu Lys Ile Ile Glu Gln Leu Pro Ser
        300                 305                 310 gct aaa gaa agt cct gat aag ttt ctg gaa gtt tgt acc tgg gta gat     2442
Ala Lys Glu Ser Pro Asp Lys Phe Leu Glu Val Cys Thr Trp Val Asp
    315                 320                 325 caa att gct gct ttg aac gat agc aaa aca cgt aag act aca agt gag     2490
Gln Ile Ala Ala Leu Asn Asp Ser Lys Thr Arg Lys Thr Thr Ser Glu
330                 335                 340                 345 aca gtg aga gct gtt ttg gat tct cta tcc gag aaa aaa aag agc tca     2538
Thr Val Arg Ala Val Leu Asp Ser Leu Ser Glu Lys Lys Lys Ser Ser
                350                 355                 360 cca tgattcccag ataagggaat tagggttcct atagggtttc gctcatgtgt         2591
Pro tgagcatata agaaaccctt agtatgtatt tgtatttgta aaatacttct atcaataaaa   2651
tttctaattc ctaaaaccaa atccagcct gcaggtctag ataaggggga tatcacgtga    2711
agcttgcaag ctccagcttt tgttcccttt agtgagggtt aattgcgcgc ttggcgtaat   2771
catggtcata gctgtttcct gtgtgaaatt gttatccgct cacaattcca cacaacatac   2831
gagccggaag cataaagtgt aaagcctggg gtgcctaatg agtgagctaa ctcacattaa   2891
ttgcgttgcg ctcactgccc gctttccagt cgggaaacct gtcgtgccag ctgcattaat   2951
gaatcggcca acgcgcgggg agaggcggtt tgcgtattgg gcgctcttcc gcttcctcgc   3011
tcactgactc gctgcgctcg gtcgttcggc tgcggcgagc ggtatcagct cactcaaagg   3071
cggtaatacg gttatccaca gaatcagggg ataacgcagg aaagaacatg tgagcaaaag   3131
gccagcaaaa ggccaggaac cgtaaaaagg ccgcgttgct ggcgtttttc cataggctcc   3191
gcccccctga cgagcatcac aaaaatcgac gctcaagtca gaggtggcga acccgacag    3251 gactataaag ataccaggcg tttccccctg gaagctccct cgtgcgctct cctgttccga   3311
ccctgccgct taccggatac ctgtccgcct ttctcccttc gggaagcgtg gcgctttctc   3371
atagctcacg ctgtaggtat ctcagttcgg tgtaggtcgt tcgctccaag ctgggctgtg   3431
tgcacgaacc ccccgttcag cccgaccgct gcgccttatc cggtaactat cgtcttgagt   3491
ccaacccggt aagacacgac ttatcgccac tggcagcagc cactggtaac aggattagca   3551
gagcgaggta tgtaggcggt gctacagagt tcttgaagtg gtggcctaac tacggctaca   3611
ctagaaggac agtatttggt atctgcgctc tgctgaagcc agttaccttc ggaaaaagag   3671
ttggtagctc ttgatccggc aaacaaacca ccgctggtag cggtggtttt tttgtttgca   3731
agcagcagat tacgcgcaga aaaaaaggat ctcaagaaga tcctttgatc ttttctacgg   3791
```

```
ggtctgacgc tcagtggaac gaaaactcac gttaagggat tttggtcatg agattatcaa   3851
aaaggatctt cacctagatc cttttaaatt aaaaatgaag ttttaaatca atctaaagta   3911
tatatgagta aacttggtct gacagttacc aatgcttaat cagtgaggca cctatctcag   3971
cgatctgtct atttcgttca tccatagttg cctgactccc cgtcgtgtag ataactacga   4031
tacgggaggg cttaccatct ggccccagtg ctgcaatgat accgcgagat ccacgctcac   4091
cggctccaga tttatcagca ataaaccagc cagccggaag ggccgagcgc agaagtggtc   4151
ctgcaacttt atccgcctcc atccagtcta ttaattgttg ccgggaagct agagtaagta   4211
gttcgccagt taatagtttg cgcaacgttg ttgccattgc tacaggcatc gtggtgtcac   4271
gctcgtcgtt tggtatggct tcattcagct ccggttccca acgatcaagg cgagttacat   4331
gatcccccat gttgtgcaaa aaagcggtta gctccttcgg tcctccgatc gttgtcagaa   4391
gtaagttggc cgcagtgtta tcactcatgg ttatggcagc actgcataat tctcttactg   4451
tcatgccatc cgtaagatgc ttttctgtga ctggtgagta ctcaaccaag tcattctgag   4511
aatagtgtat gcggcgaccg agttgctctt gcccggcgtc aatacgggat aataccgcgc   4571
cacatagcag aactttaaaa gtgctcatca ttggaaaacg ttcttcgggg cgaaaactct   4631
caaggatctt accgctgttg agatccagtt cgatgtaacc cactcgtgca cccaactgat   4691
cttcagcatc ttttactttc accagcgttt ctgggtgagc aaaaacagga aggcaaaatg   4751
ccgcaaaaaa gggaataagg gcgacacgga aatgttgaat actcatactc ttcctttttc   4811
aatattattg aagcatttat cagggttatt gtctcatgag cggatacata tttgaatgta   4871
tttagaaaaa taaacaaata ggggttccgc gcacatttcc ccgaaaagtg ccac         4925
```

<210> SEQ ID NO 7
<211> LENGTH: 362
<212> TYPE: PRT
<213> ORGANISM: Artificial
<220> FEATURE:
<223> OTHER INFORMATION: Synthetic Construct

<400> SEQUENCE: 7

```
Met Ala Lys Pro Pro Lys Lys Arg Lys Val His Met Asn Thr Lys
1               5                   10                  15

Tyr Asn Lys Glu Phe Leu Leu Tyr Leu Ala Gly Phe Val Asp Gly Asp
            20                  25                  30

Gly Ser Ile Ile Ala Gln Ile Lys Pro Asn Gln Ser Cys Lys Phe Lys
        35                  40                  45

His Gln Leu Met Leu Thr Phe Gln Val Thr Gln Lys Thr Gln Arg Arg
    50                  55                  60

Trp Phe Leu Asp Lys Leu Val Asp Glu Ile Gly Val Gly Lys Val Tyr
65                  70                  75                  80

Asp Arg Gly Ser Val Ser Asp Tyr Arg Leu Cys Gln Ile Lys Pro Leu
                85                  90                  95

His Asn Phe Leu Thr Gln Leu Gln Pro Phe Leu Lys Leu Lys Gln Lys
            100                 105                 110

Gln Ala Asn Leu Val Leu Lys Ile Ile Glu Gln Leu Pro Ser Ala Lys
        115                 120                 125

Glu Ser Pro Asp Lys Phe Leu Glu Val Cys Thr Trp Val Asp Gln Ile
    130                 135                 140

Ala Ala Leu Asn Asp Ser Lys Thr Arg Lys Thr Thr Ser Glu Thr Val
145                 150                 155                 160
```

-continued

```
Arg Ala Val Leu Asp Ser Leu Pro Gly Ser Val Gly Gly Leu Ser Pro
                165                 170                 175
Ser Gln Ala Ser Ser Ala Ala Ser Ser Ala Ser Ser Pro Gly Ser
        180                 185                 190
Gly Ile Ser Glu Ala Leu Arg Ala Gly Ala Thr Lys Ser Lys Glu Phe
            195                 200                 205
Leu Leu Tyr Leu Ala Gly Phe Val Asp Gly Asp Gly Ser Ile Lys Ala
    210                 215                 220
Gln Ile Ser Pro Glu Gln Ser Arg Lys Phe Lys His Arg Leu Arg Leu
225                 230                 235                 240
Thr Phe Gln Val Thr Gln Lys Thr Gln Arg Arg Trp Phe Leu Asp Lys
                245                 250                 255
Leu Val Asp Glu Ile Gly Val Gly Lys Val Tyr Asp Ser Gly Ser Val
                260                 265                 270
Ser Asp Tyr Ile Leu Ser Gln Ile Lys Pro Leu His Asn Phe Leu Thr
        275                 280                 285
Gln Leu Gln Pro Phe Leu Lys Leu Lys Gln Lys Gln Ala Asn Leu Val
    290                 295                 300
Leu Lys Ile Ile Glu Gln Leu Pro Ser Ala Lys Glu Ser Pro Asp Lys
305                 310                 315                 320
Phe Leu Glu Val Cys Thr Trp Val Asp Gln Ile Ala Ala Leu Asn Asp
                325                 330                 335
Ser Lys Thr Arg Lys Thr Thr Ser Glu Thr Val Arg Ala Val Leu Asp
                340                 345                 350
Ser Leu Ser Glu Lys Lys Lys Ser Pro
        355                 360

<210> SEQ ID NO 8
<211> LENGTH: 163
<212> TYPE: PRT
<213> ORGANISM: Artificial
<220> FEATURE:
<223> OTHER INFORMATION: I-CreI natural variant

<400> SEQUENCE: 8

Met Asn Thr Lys Tyr Asn Lys Glu Phe Leu Leu Tyr Leu Ala Gly Phe
1               5                   10                  15
Val Asp Gly Asp Gly Ser Ile Ile Ala Gln Ile Lys Pro Asn Gln Ser
            20                  25                  30
Tyr Lys Phe Lys His Gln Leu Ser Leu Thr Phe Gln Val Thr Glu Lys
        35                  40                  45
Thr Gln Arg Arg Trp Phe Leu Asp Lys Leu Val Asp Glu Ile Gly Val
    50                  55                  60
Gly Tyr Val Arg Asp Arg Gly Ser Val Ser Asp Tyr Ile Leu Ser Glu
65                  70                  75                  80
Ile Lys Pro Leu His Asn Phe Leu Thr Gln Leu Gln Pro Phe Leu Lys
                85                  90                  95
Leu Lys Gln Lys Gln Ala Asn Leu Val Leu Lys Ile Ile Glu Gln Leu
            100                 105                 110
Pro Ser Ala Lys Glu Ser Pro Asp Lys Phe Leu Glu Val Cys Thr Trp
        115                 120                 125
Val Asp Gln Ile Ala Ala Leu Asn Asp Ser Lys Thr Arg Lys Thr Thr
    130                 135                 140
Ser Glu Thr Val Arg Ala Val Leu Asp Ser Leu Ser Glu Lys Lys Lys
145                 150                 155                 160
```

Ser Ser Pro

<210> SEQ ID NO 9
<211> LENGTH: 360
<212> TYPE: PRT
<213> ORGANISM: Artificial sequence
<220> FEATURE:
<223> OTHER INFORMATION: BAY 35-36 single chain meganuclease

<400> SEQUENCE: 9

```
Met Ala Pro Lys Lys Arg Lys Val His Met Asn Thr Lys Tyr Asn
1               5                   10                  15

Lys Glu Phe Leu Leu Tyr Leu Ala Gly Phe Val Asp Gly Asp Gly Ser
            20                  25                  30

Ile Ile Ala Gln Ile Lys Pro Asn Gln Ser Cys Lys Phe Lys His Gln
        35                  40                  45

Leu Met Leu Thr Phe Gln Val Thr Gln Lys Thr Gln Arg Arg Trp Phe
    50                  55                  60

Leu Asp Lys Leu Val Asp Glu Ile Gly Val Gly Lys Val Tyr Asp Arg
65                  70                  75                  80

Gly Ser Val Ser Asp Tyr Arg Leu Cys Gln Ile Lys Pro Leu His Asn
                85                  90                  95

Phe Leu Thr Gln Leu Gln Pro Phe Leu Lys Leu Lys Gln Lys Gln Ala
            100                 105                 110

Asn Leu Val Leu Lys Ile Ile Glu Gln Leu Pro Ser Ala Lys Glu Ser
        115                 120                 125

Pro Asp Lys Phe Leu Glu Val Cys Thr Trp Val Asp Gln Ile Ala Ala
    130                 135                 140

Leu Asn Asp Ser Lys Thr Arg Lys Thr Thr Ser Glu Thr Val Arg Ala
145                 150                 155                 160

Val Leu Asp Ser Leu Pro Gly Ser Val Gly Gly Leu Ser Pro Ser Gln
                165                 170                 175

Ala Ser Ser Ala Ala Ser Ser Ala Ser Ser Ser Pro Gly Ser Gly Ile
            180                 185                 190

Ser Glu Ala Leu Arg Ala Gly Ala Thr Lys Ser Lys Glu Phe Leu Leu
        195                 200                 205

Tyr Leu Ala Gly Phe Val Asp Gly Asp Gly Ser Ile Lys Ala Gln Ile
    210                 215                 220

Ser Pro Glu Gln Ser Arg Lys Phe Lys His Arg Leu Arg Leu Thr Phe
225                 230                 235                 240

Gln Val Thr Gln Lys Thr Gln Arg Arg Trp Phe Leu Asp Lys Leu Val
                245                 250                 255

Asp Glu Ile Gly Val Gly Lys Val Tyr Asp Ser Gly Ser Val Ser Asp
            260                 265                 270

Tyr Ile Leu Ser Gln Ile Lys Pro Leu His Asn Phe Leu Thr Gln Leu
        275                 280                 285

Gln Pro Phe Leu Lys Leu Lys Gln Lys Gln Ala Asn Leu Val Leu Lys
    290                 295                 300

Ile Ile Glu Gln Leu Pro Ser Ala Lys Glu Ser Pro Asp Lys Phe Leu
305                 310                 315                 320

Glu Val Cys Thr Trp Val Asp Gln Ile Ala Ala Leu Asn Asp Ser Lys
                325                 330                 335

Thr Arg Lys Thr Thr Ser Glu Thr Val Arg Ala Val Leu Asp Ser Leu
            340                 345                 350

Ser Glu Lys Lys Lys Ser Ser Pro
```

```
                    355                 360

<210> SEQ ID NO 10
<211> LENGTH: 9
<212> TYPE: PRT
<213> ORGANISM: Artificial sequence
<220> FEATURE:
<223> OTHER INFORMATION: I-CreI endonuclease motif

<400> SEQUENCE: 10

Leu Ala Gly Leu Ile Asp Ala Asp Gly
1               5
```